US 11,883,081 B2

(12) United States Patent
Hyer et al.

(10) Patent No.: US 11,883,081 B2
(45) Date of Patent: Jan. 30, 2024

(54) FASTENING DEVICES, SYSTEMS, AND METHODS

(71) Applicant: RTG Scientific, LLC, Austin, TX (US)

(72) Inventors: Richard Justin Hyer, Hyrum, UT (US); Jonathan Bitter, Hyde Park, UT (US)

(73) Assignee: RTG Scientific, LLC, Austin, TX (US)

( * ) Notice: Subject to any disclaimer, the term of this patent is extended or adjusted under 35 U.S.C. 154(b) by 244 days.

(21) Appl. No.: 17/314,028

(22) Filed: May 6, 2021

(65) Prior Publication Data

US 2022/0151670 A1    May 19, 2022

Related U.S. Application Data

(60) Provisional application No. 63/147,640, filed on Feb. 9, 2021, provisional application No. 63/116,092, filed on Nov. 19, 2020.

(51) Int. Cl.
*A61B 17/86*    (2006.01)
*B23G 1/32*    (2006.01)
(Continued)

(52) U.S. Cl.
CPC ........ *A61B 17/8625* (2013.01); *A61B 17/866* (2013.01); *B23G 1/32* (2013.01);
(Continued)

(58) Field of Classification Search
CPC ... A61B 17/8625; A61B 17/86; A61B 17/863; A61B 2017/8655; F16B 33/02
(Continued)

(56) References Cited

U.S. PATENT DOCUMENTS 3,848,276 A    11/1974  Martinez
4,810,149 A *  3/1989   Lee .................. F16B 33/02
                                                411/366.3
(Continued)

FOREIGN PATENT DOCUMENTS

GB         2033755 A      5/1980
WO      2004098442 A1    11/2004
(Continued)

OTHER PUBLICATIONS

Scortecci et al., "Dental Implantology Device," WO2006117298, Machine Translation, retrieved Mar. 11, 2023 (Year: 2023).*
(Continued)

*Primary Examiner* — Kevin T Truong
*Assistant Examiner* — Tracy L Kamikawa
(74) *Attorney, Agent, or Firm* — David Meibos; Maywood IP Law

(57) ABSTRACT

A fastener with improved threading for resisting multi-axial forces and off-axis loading scenarios is provided. The fastener may include a shaft and a plurality of helical threads disposed about the shaft. The plurality of helical threads may include a first helical thread and a second helical thread adjacent the first helical thread. The first helical thread may include a first concave undercut surface and a first convex undercut surface. The second helical thread may include a second concave undercut surface and a second convex undercut surface. When the fastener is viewed in section along a plane intersecting a longitudinal axis of the shaft, the first concave undercut surface and the second convex undercut surface may be oriented toward the proximal end of the shaft, and the first convex undercut surface and the second concave undercut surface may be oriented toward the distal end of the shaft.

19 Claims, 15 Drawing Sheets

(51) Int. Cl.
*B23G 5/18* (2006.01)
*A61C 8/00* (2006.01)
*A61B 17/00* (2006.01)

(52) U.S. Cl.
CPC ...... *B23G 5/18* (2013.01); *A61B 2017/00526* (2013.01); *A61C 8/0025* (2013.01); *B23G 2200/48* (2013.01)

(58) Field of Classification Search
USPC .................................................. 411/411, 412
See application file for complete search history.

(56) References Cited

U.S. PATENT DOCUMENTS

| | | | |
|---|---|---|---|
| 5,964,768 A | 10/1999 | Huebner | |
| 6,800,078 B2 * | 10/2004 | Reed | A61B 17/7038 |
| | | | 606/308 |
| 7,537,603 B2 | 5/2009 | Huebner et al. | |
| 8,337,205 B2 | 12/2012 | Reed | |
| 8,602,781 B2 * | 12/2013 | Reed | A61C 8/0022 |
| | | | 606/301 |
| 8,875,399 B2 | 11/2014 | Reed | |
| 9,079,263 B2 * | 7/2015 | Reed | A61B 17/8635 |
| 9,526,547 B2 | 12/2016 | Reed | |
| 9,687,319 B2 | 6/2017 | Reed | |
| 9,782,209 B2 | 10/2017 | Reed | |
| 9,901,379 B2 * | 2/2018 | Reed | A61B 17/866 |
| 10,085,782 B2 * | 10/2018 | Reed | A61B 17/864 |
| 10,265,177 B2 | 4/2019 | Quinn et al. | |
| 10,441,385 B2 | 10/2019 | Reed | |
| 10,639,086 B2 | 5/2020 | Reed | |
| 10,687,877 B2 | 6/2020 | Lavigne et al. | |
| 2006/0204930 A1 * | 9/2006 | Sul | A61C 8/0022 |
| | | | 433/174 |
| 2007/0233123 A1 | 10/2007 | Ahmad et al. | |
| 2008/0286720 A1 * | 11/2008 | Reed | A61C 8/0074 |
| | | | 433/174 |
| 2010/0094358 A1 | 4/2010 | Moore et al. | |
| 2010/0121327 A1 | 5/2010 | Velikov | |
| 2011/0288650 A1 | 11/2011 | Ries et al. | |
| 2014/0023990 A1 * | 1/2014 | Zadeh | A61C 8/0022 |
| | | | 433/174 |
| 2014/0058460 A1 | 2/2014 | Reed | |
| 2014/0329202 A1 | 11/2014 | Zadeh | |
| 2018/0303529 A1 | 10/2018 | Zastrozna | |
| 2018/0335070 A1 * | 11/2018 | May | F16B 33/02 |
| 2019/0038426 A1 | 2/2019 | Ek | |
| 2019/0105131 A1 * | 4/2019 | Barton | A61C 8/0025 |
| 2019/0358039 A1 | 11/2019 | Ducharme et al. | |
| 2021/0259842 A1 | 8/2021 | Feng et al. | |
| 2022/0152715 A1 * | 5/2022 | Hyer | B23G 5/18 |

FOREIGN PATENT DOCUMENTS

| | | | | |
|---|---|---|---|---|
| WO | WO-2006117298 A1 * | 11/2006 | ........... | A61C 8/0022 |
| WO | 2007074498 A2 | 7/2007 | | |
| WO | 2020224657 A1 | 11/2020 | | |

OTHER PUBLICATIONS

International Search Report and Written Opinion dated Apr. 25, 2022 for corresponding PCT Application No. PCT/US2021/060196.
International Search Report and Written Opinion dated Jul. 6, 2022 for corresponding PCT Application No. PCT/US2022/015866.
International Search Report and Written Opinion dated Mar. 2, 2022 for corresponding PCT Application No. PCT/US2021/060175.
International Search Report dated Aug. 10, 2023 for corresponding PCT/US2023/020900.
International Search Report dated Jul. 5, 2023 for corresponding PCT/US2023/018561.
Office Action dated Aug. 29, 2023 for corresponding U.S. Appl. No. 17/877,918.

* cited by examiner

FASTENING DEVICES, SYSTEMS, AND METHODS

CROSS-REFERENCE TO RELATED APPLICATIONS

This application claims the benefit of U.S. Provisional Patent Application Ser. No. 63/116,092 filed on Nov. 19, 2020, entitled "FASTENING SYSTEMS AND METHODS", and U.S. Provisional Patent Application Ser. No. 63/147,640 filed on Feb. 9, 2021, entitled "FASTENING DEVICES, SYSTEMS, AND METHODS". The above-referenced documents are hereby incorporated by reference in their entirety.

TECHNICAL FIELD

The present disclosure relates to fastening devices, systems, and methods. More specifically, the present disclosure relates to fastening devices with improved thread designs, fastening systems utilizing fastening devices with improved thread designs, and methods of manufacturing fasteners with improved thread designs.

BACKGROUND

Surgical procedures involving fasteners implanted within bone and other tissues can become lose over time due to multi-axial forces and off-axis loading scenarios that may be applied to the fastener during the healing process. Traditional fastener thread designs may not provide sufficient fastener fixation to overcome these multi-axial forces and off-axis loading scenarios.

Accordingly, fasteners with improved thread designs for increasing bone fixation and load sharing between a bone/fastener interface experiencing multi-axial and off-loading conditions, as well as improved methods for manufacturing such fasteners, would be desirable.

SUMMARY

The various fastening devices, systems, and methods of the present disclosure have been developed in response to the present state of the art, and in particular, in response to the problems and needs in the art that have not yet been fully solved by currently available fastening devices, systems, and methods. In some embodiments, the fastening devices, systems, and methods of the present disclosure may provide improved bone fixation and load sharing between a bone/fastener interface under multi-axial and off-loading conditions.

In some embodiments, an implantable bone anchor may include a shaft, a first helical thread and a second helical thread. The shaft may include a proximal end, a distal end, and a longitudinal axis. The first helical thread may be disposed about the shaft along the longitudinal axis between the proximal and distal ends of the shaft. The first helical thread may include a first undercut surface, a second undercut surface, a third undercut surface, and a fourth open surface. The second helical thread may also be disposed about the shaft adjacent the first helical thread. The second helical thread may include a fifth undercut surface, a sixth undercut surface, a seventh undercut surface, and an eighth open surface. The first undercut surface, the third undercut surface, the sixth undercut surface, and the eighth open surface may be angled towards the distal end of the shaft. The second undercut surface, the fourth open surface, the fifth undercut surface, and the seventh undercut surface may be angled towards the proximal end of the shaft.

In some embodiments of the implantable bone anchor, when the implantable bone anchor is viewed in section along a plane intersecting the longitudinal axis of the shaft, the first helical thread may include at least one chevron shape oriented toward the distal end of the shaft, and the second helical thread may include at least one chevron shape oriented toward the proximal end of the shaft.

In some embodiments of the implantable bone anchor, the first helical thread may include a first plurality of chevron shapes oriented toward the distal end of the shaft, and the second helical thread may include a second plurality of chevron shapes oriented toward the proximal end of the shaft.

In some embodiments of the implantable bone anchor, the first plurality of chevron shapes and the second plurality of chevron shapes may be arranged in alternating succession along the shaft of the implantable bone anchor.

In some embodiments of the implantable bone anchor, when the implantable bone anchor is viewed in section along a plane intersecting the longitudinal axis of the shaft, the first helical thread may include at least one partial crescent shape oriented toward the distal end of the shaft, and the second helical thread may include at least one partial crescent shape oriented toward the proximal end of the shaft.

In some embodiments of the implantable bone anchor, the first helical thread may include a first plurality of partial crescent shapes oriented toward the distal end of the shaft, and the second helical thread may include a second plurality of partial crescent shapes oriented toward the proximal end of the shaft.

In some embodiments of the implantable bone anchor, the first plurality of partial crescent shapes and the second plurality of partial crescent shapes may be arranged in alternating succession along the shaft of the implantable bone anchor.

In some embodiments, a fastener may include a shaft and a plurality of helical threads. The shaft may include a proximal end, a distal end, and a longitudinal axis. The plurality of helical threads may be disposed about the shaft along the longitudinal axis between the proximal and distal ends of the shaft. The plurality of helical threads may include a first helical thread and a second helical thread. The first helical thread may include a first concave undercut surface and a first convex undercut surface. The second helical thread may include a second concave undercut surface and a second convex undercut surface. The first concave undercut surface and the second convex undercut surface may be oriented toward the proximal end of the shaft. The first convex undercut surface and the second concave undercut surface may be oriented toward the distal end of the shaft.

In some embodiments of the fastener, the plurality of helical threads may include three helical threads.

In some embodiments of the fastener, the plurality of helical threads may include four helical threads.

In some embodiments of the fastener, the plurality of helical threads may include more than four helical threads.

In some embodiments of the fastener, at least one of the first concave undercut surface, the first convex undercut surface, the second concave undercut surface, and the second convex undercut surface may include at least one substantially flat surface.

In some embodiments of the fastener, at least one of the first concave undercut surface, the first convex undercut surface, the second concave undercut surface, and the second convex undercut surface may include at least one curved surface.

In some embodiments of the fastener, when the fastener is viewed in section along a plane intersecting the longitudinal axis of the shaft, the first helical thread may include a first bent shape with a first intermediate portion oriented toward the distal end of the shaft, and the second helical thread may include a second bent shape with a second intermediate portion oriented toward the proximal end of the shaft.

In some embodiments of the fastener, when the fastener is viewed in section along a plane intersecting the longitudinal axis of the shaft, a first interlocking space may be formed intermediate the first concave undercut surface and the second concave undercut surface, and a second interlocking space may be formed intermediate the first convex undercut surface and the second convex undercut surface. Each of the first interlocking space and the second interlocking space may be configured to receive bone tissue therein and each of the first interlocking space and the second interlocking space may be shaped to interlock with the bone tissue to increase fixation of the fastener within the bone tissue.

In some embodiments of the fastener, the first interlocking space may be larger in size than the second interlocking space.

In some embodiments, an implantable bone anchor may have a shaft with a proximal end, a distal end, and a longitudinal axis. The implantable bone anchor may also have a first helical thread disposed about the shaft along the longitudinal axis between the proximal and distal ends of the shaft. The first helical thread may have a first proximally-oriented surface facing toward the proximal end, and a first distally-oriented surface facing toward the distal end. The implantable bone anchor may also have a second helical thread disposed about the shaft adjacent the first helical thread. The second helical thread may have a second proximally-oriented surface facing toward the proximal end, and a second distally-oriented surface facing toward the distal end. The first proximally-oriented surface and the first distally-oriented surface may not have mirror symmetry relative to each other across any plane perpendicular to the longitudinal axis. The first proximally-oriented surface and the second distally-oriented surface may have mirror symmetry relative to each other across a first plane perpendicular to the longitudinal axis.

The first proximally-oriented surface may be generally concave. The second distally-oriented surface may be generally convex.

The second proximally-oriented surface may be generally convex. The first distally-oriented surface may be generally concave.

The second proximally-oriented surface and the second distally-oriented surface may not have mirror symmetry relative to each other across any plane perpendicular to the longitudinal axis. The second proximally-oriented surface and the first distally-oriented surface may have mirror symmetry relative to each other across a second plane perpendicular to the longitudinal axis.

These and other features and advantages of the present disclosure will become more fully apparent from the following description and appended claims, or may be learned by the practice of the instruments, systems, and methods set forth hereinafter.

BRIEF DESCRIPTION OF THE DRAWINGS

Exemplary embodiments of the present disclosure will become more fully apparent from the following description taken in conjunction with the accompanying drawings. Understanding that these drawings depict only exemplary embodiments and are, therefore, not to be considered limiting of the scope of the present disclosure, the exemplary embodiments of the present disclosure will be described with additional specificity and detail through use of the accompanying drawings in which.

Figure 1A:
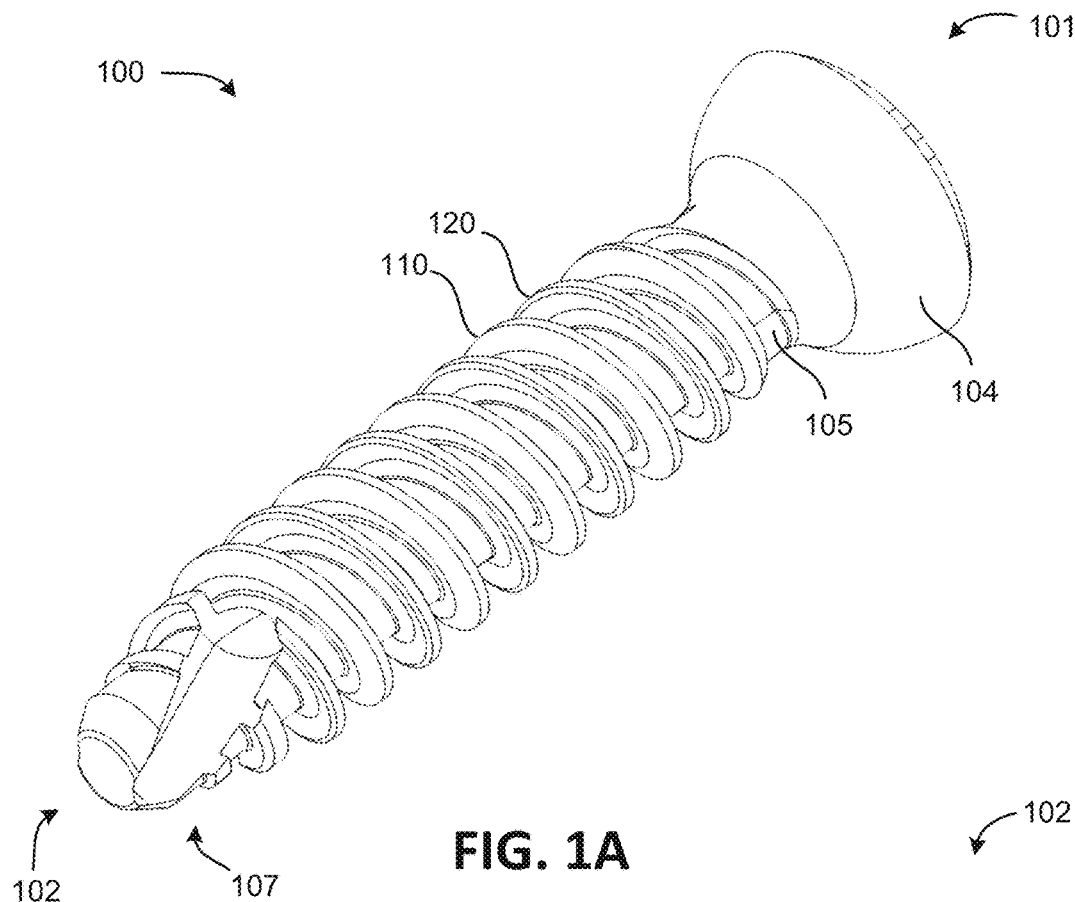
FIG. 1A illustrates a front perspective view of a fastener, according to an embodiment of the present disclosure.

It is to be understood that the drawings are for purposes of illustrating the concepts of the present disclosure and may not be drawn to scale. Furthermore, the drawings illustrate exemplary embodiments and do not represent limitations to the scope of the present disclosure.

DETAILED DESCRIPTION

Exemplary embodiments of the present disclosure will be best understood by reference to the drawings, wherein like parts are designated by like numerals throughout. It will be readily understood that the components of the present disclosure, as generally described and illustrated in the drawings, could be arranged, and designed in a wide variety of different configurations. Thus, the following more detailed description of the embodiments of the implants, systems, and methods, as represented in the drawings, is not intended to limit the scope of the present disclosure, but is merely representative of exemplary embodiments of the present disclosure.

The word "exemplary" is used herein to mean "serving as an example, instance, or illustration." Any embodiment described herein as "exemplary" is not necessarily to be construed as preferred or advantageous over other embodiments. While the various aspects of the embodiments are presented in the drawings, the drawings are not necessarily drawn to scale unless specifically indicated.

The following disclosure presents various fasteners for utilization in bone and other tissues as implantable devices (e.g., orthopedic implants, spine implants, sports medicine implants, dental implants, trauma implants, reconstruction implants, extremity implants, craniomaxillofacial (CMF) implants, veterinary implants, etc.) for the purpose of streamlining the present disclosure. However, it will be understood that the various fasteners and helical threading concepts presented herein can be utilized in any medium beyond bones/tissues and/or for any application beyond surgical procedures.

Example applications/procedures that may utilize any of the fasteners described or contemplated herein, in any configuration and with any of the features described herein, may include, but are not limited to: trauma procedures, spine procedures (e.g., SI fusion, facet fixation, etc.), reconstruction procedures, sports related procedures, ACL/tenodesis procedures, extremity procedures, dental procedures, CMF procedures, veterinary procedures, fracture fixation plate procedures (e.g., distal femur plates, proximal humerus plates, tibial plates, etc.), supplemental Fixation for IBD procedures, intramedullary canal fixation procedures, nail fixation procedures, limb salvage and transfemoral procedures, amputee connection procedures, total shoulder fixation, reverse glenoid fixation, small bone fixation (e.g., podiatric, hand/wrist, etc.), joint fusions, single-tooth implant fixation, jaw/facial reconstruction, dentures fixation, veterinary trauma, species specific procedures (e.g., equine, canine, rabbit, etc.), TPLO, shear fixation, osteotomies, fusions, procedures involving osteoporotic or compromised bone, etc.

Moreover, fastener types that may utilize any of the thread designs, morphology, and/or features described herein may include, but are not limited to: cortical fasteners, soft tissue fasteners, long fasteners, cannulated fasteners, plate fasteners, locking/non-locking fasteners, dynamic hip fasteners, acetabular cup fasteners, Schanz pins, half pins, pedicle fasteners, cervical fasteners, threaded stems, threaded intramedullary canal stems, joint stems, revision fasteners, compression fasteners (e.g., headless/headed compression fasteners, hip compression fasteners, etc.), ACL fasteners, tenodesis fasteners, bone-tendon-bone graft fasteners, suture anchors, dental fasteners, mandibular tenting fasteners, veterinary fasteners, etc.

Figure 1B:
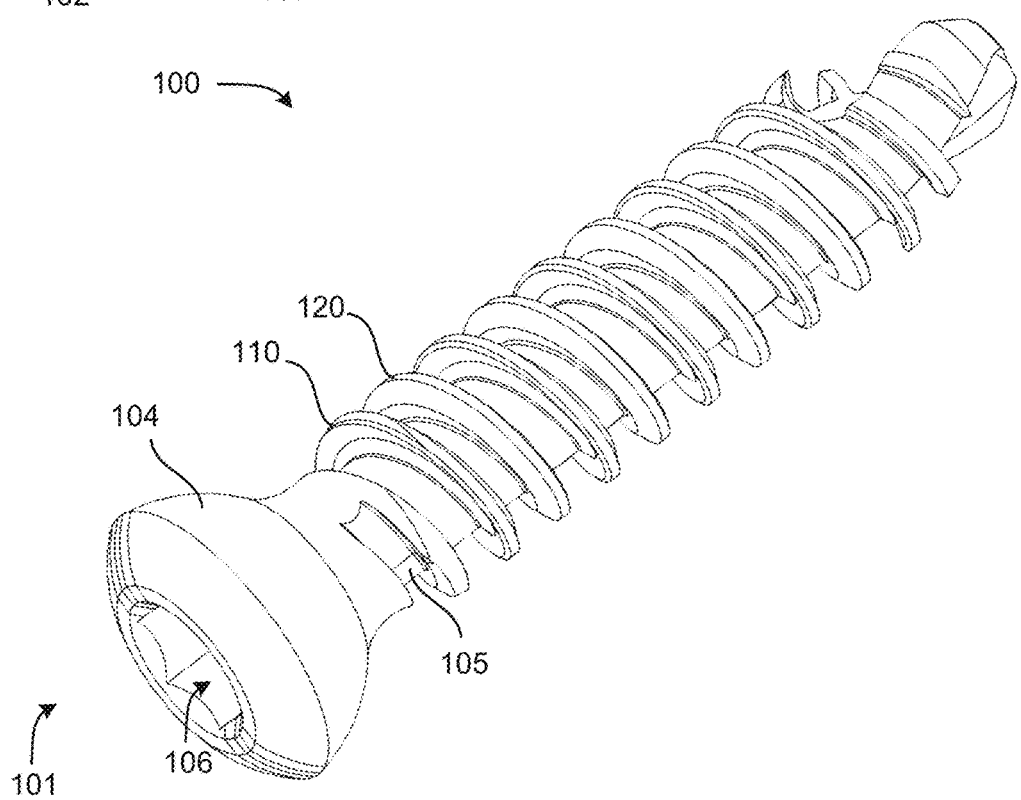
FIG. 1B illustrates a rear perspective view of the fastener of FIG. 1A.
Figure 1C:
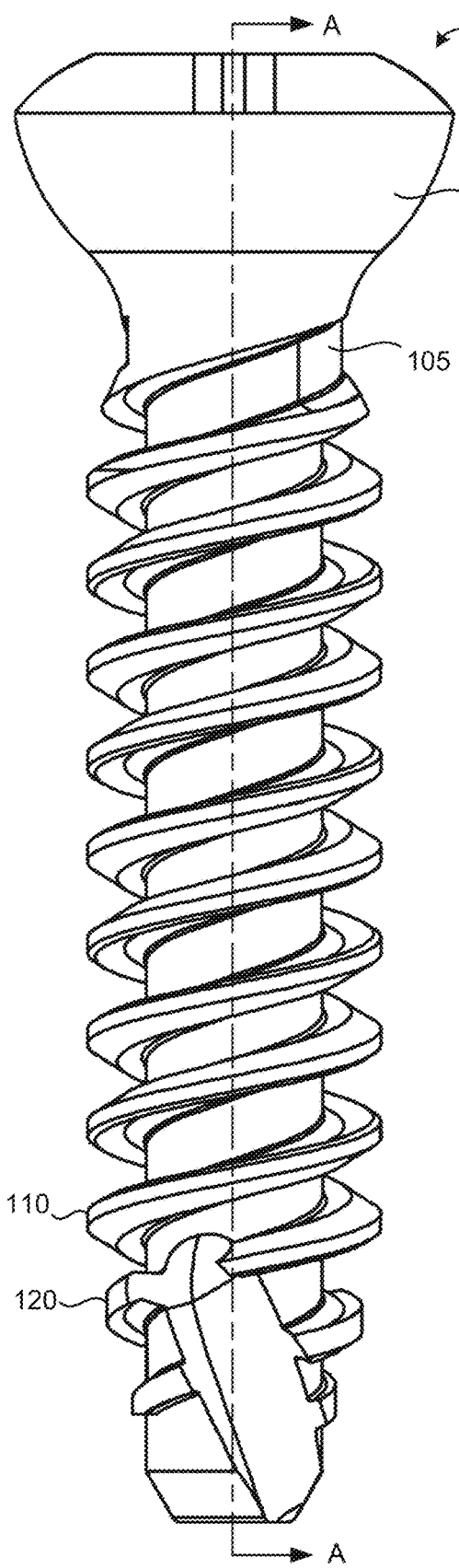
FIG. 1C illustrates a side view of the fastener of FIG. 1A.
Figure 1D:
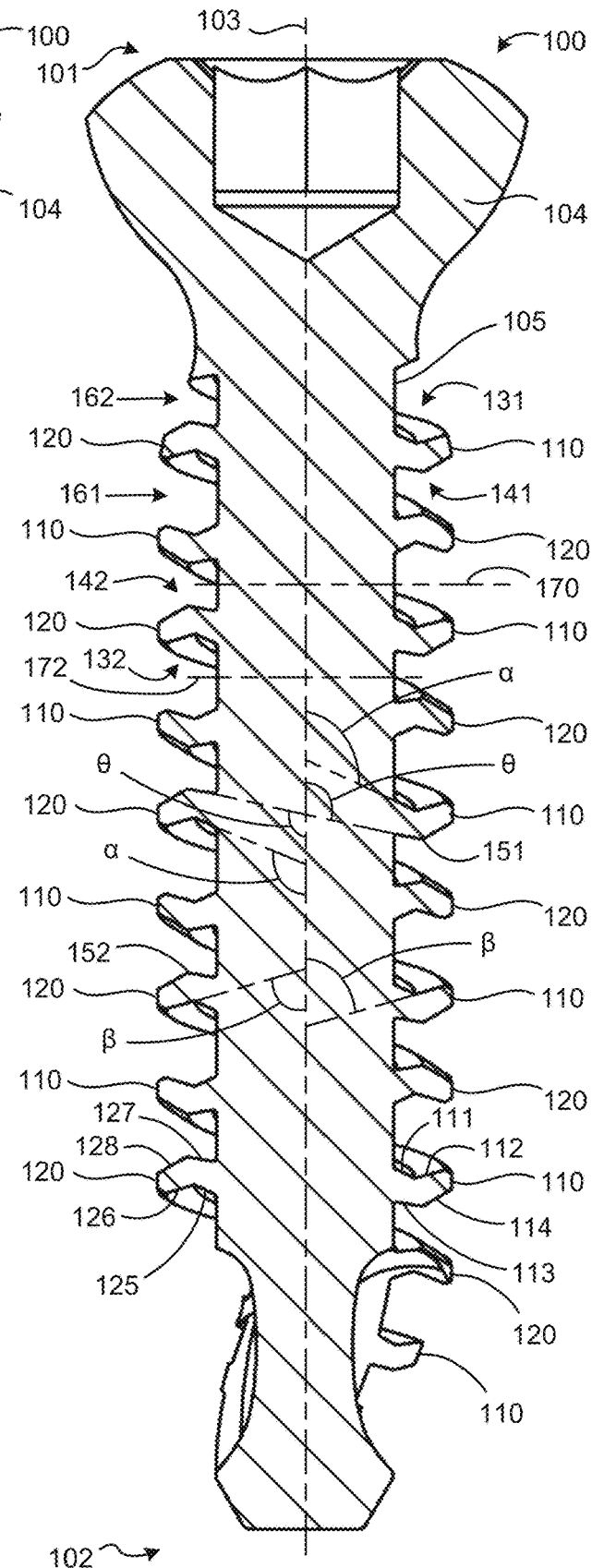
FIG. 1D illustrates a cross-sectional side view of the fastener of FIG. 1A taken along the line A-A shown in FIG. 1C.

FIGS. 1A-D illustrate various views of a fastener 100, implantable bone anchor, or bone screw, according to one embodiment of the present disclosure. Specifically, FIG. 1A is a front perspective view of the fastener 100, FIG. 1B is a rear perspective view of the fastener 100, FIG. 1C is a side view of the fastener 100, and FIG. 1D is a cross-sectional side view of the fastener 100 taken along the line A-A in FIG. 1C.

In general, the fastener 100 may include a shaft 105 having a proximal end 101, a distal end 102, and a longitudinal axis 103. The fastener 100 may also include a head 104 located at the proximal end 101 of the shaft 105, a torque connection interface 106 formed in/on the head 104 (in either a male/female configuration), and a self-tapping feature 107 formed in the distal end 102 of the shaft 105.

In some embodiments, the fastener 100 may include a first helical thread 110 disposed about the shaft 105, and a second helical thread 120 disposed about the shaft 105 adjacent the first helical thread 110.

In some embodiments, the fastener 100 may include a "dual start" or "dual lead" thread configuration comprising the first helical thread 110 and the second helical thread 120.

In some embodiments, a depth of the first helical thread 110 and/or the second helical thread 120 with respect to the shaft 105 may define a major diameter vs. a minor diameter of the shaft 105 alone.

In some embodiments, a major diameter and/or a minor diameter of the fastener 100 may be constant or substantially constant along the entire length of the fastener, or along a majority of the length of the fastener. In these embodiments, a constant minor diameter may help avoid blowout of narrow/delicate bones (e.g., a pedicle) when inserting a fastener into a bone. In some embodiments, a pilot hole may first be drilled into a narrow/delicate bone and then a fastener having a similar minor diameter in comparison to the diameter of the pilot hole may be chosen to avoid blowout when inserting the fastener into the bone.

In some embodiments, a depth of the first helical thread 110 and/or the second helical thread 120 with respect to the shaft 105 may vary along a length of the shaft 105 to define one or more major diameters of the fastener 100 and/or one or more regions along the fastener 100 may comprise a one or more continuously variable major diameters.

In some embodiments, a thickness of the shaft 105 may vary along a length of the shaft 105 to define one or more minor diameters of the fastener 100, and/or one or more regions along the fastener 100 may comprise one or more continuously variable minor diameters. In some embodiments, a thickness/height/width/length/pitch/shape of the first helical thread 110 and/or the second helical thread 120 (or any additional helical thread) may vary along a length of the shaft 105. For example, a thickness/height/width/length/pitch/shape of the first helical thread 110 and/or the second helical thread 120 may be greater towards the tip of the fastener and thinner towards the head of the fastener (or vice versa) in either a discrete or continuously variable fashion, etc.

In some embodiments, the major and/or minor diameters may increase toward a proximal end or head of a fastener in order to increase bone compaction as the fastener is terminally inserted into the bone/tissue.

In some embodiments, a pitch of the first helical thread 110 and/or the second helical thread 120 may vary along a length of the fastener 100.

In some embodiments, the fastener 100 may include a plurality of helical threads disposed about the shaft 105. However, it will also be understood that any of the fasteners disclosed or contemplated herein may include a single helical thread disposed about the shaft of the fastener. Moreover, the fastener 100 may comprise a nested plurality of helical threads having different lengths (not shown). As one non-limiting example, the fastener 100 may include a first helical thread 110 that is longer than a second helical thread 120, such that the fastener 100 comprises dual threading along a first portion of the shaft 105 and single threading along a second portion of the shaft 105.

In some embodiments, the plurality of helical threads may include three helical threads (not shown) comprising a "triple start" or "triple lead" thread configuration (not shown).

In some embodiments, the plurality of helical threads may include four helical threads (not shown) comprising a "quadruple start" or "quadruple lead" thread configuration (not shown).

In some embodiments, the plurality of helical threads may include more than four helical threads (not shown).

In some embodiments, the fastener 100 may include first threading with any of the shapes disclosed herein oriented toward one of the proximal end and the distal end of the fastener 100 with the first threading located proximate the distal end of the fastener 100, as well as second threading with any of the shapes disclosed herein oriented toward the other one of the proximal end and the distal end of the fastener 100 with the second threading located proximate the head of the fastener 100 (not shown).

In some embodiments, the fastener 100 may include multiple threading (e.g., dual helical threading, etc.) with any of the shapes disclosed herein located proximate one of the proximal end and the distal end of the fastener 100, as well as single threading with any of the shapes disclosed herein with the second threading located proximate the other of the proximal end and the distal end of the fastener 100 (not shown).

In some embodiments, the first helical thread 110 may include a plurality of first concave undercut surfaces 131 and a plurality of first convex undercut surfaces 141.

In some embodiments, the second helical thread 120 may include a plurality of second concave undercut surfaces 132 and a plurality of second convex undercut surfaces 142.

In some embodiments, when the fastener 100 is viewed in section along a plane that intersects the longitudinal axis 103 of the shaft 105 (as shown in FIG. 1D), the plurality of first concave undercut surfaces 131 and the plurality of second convex undercut surfaces 142 may be oriented toward (i.e., point toward) the proximal end 101 of the shaft 105.

In some embodiments, the plurality of first convex undercut surfaces 141 and the plurality of second concave undercut surfaces 132 may be oriented toward (i.e., point toward) the distal end 102 of the shaft 105.

In some embodiments, at least one of the plurality of first concave undercut surfaces 131, the plurality of first convex undercut surfaces 141, the plurality of second concave undercut surfaces 132, and the plurality of second convex undercut surfaces 142 may comprise at least one substantially flat surface.

In some embodiments, when the fastener 100 is viewed in section along a plane intersecting the longitudinal axis 103 of the shaft 105, the first helical thread 110 may comprise a plurality of first bent shapes (comprising at least one surface that is angled relative to the longitudinal axis 103 of the shaft 105 and/or at least one undercut surface) with a plurality of first intermediate portions 151 that are oriented toward (i.e., point toward) the distal end 102 of the shaft 105. This may be referred to as "standard" threading, having a "standard" orientation.

In some embodiments, when the fastener 100 is viewed in section along a plane intersecting the longitudinal axis 103 of the shaft 105, the second helical thread 120 may comprise a plurality of second bent shapes (comprising at least one surface that is angled relative to the longitudinal axis 103 of the shaft 105 and/or at least one undercut surface) with a plurality of second intermediate portions 152 that are oriented toward (i.e., point toward) the proximal end 101 of the shaft 105. This may be referred to as "inverted" threading, having an "inverted" orientation.

In some embodiments, one or more helical threads may morph/transition between a standard orientation and an inverted orientation along a shaft of a fastener.

In some embodiments, at least one of the plurality of first concave undercut surfaces 131, the plurality of first convex undercut surfaces 141, the plurality of second concave undercut surfaces 132, and the plurality of second convex undercut surfaces 142 may comprise at least one curved surface.

As shown in FIG. 1D, the proximally-oriented and distally-oriented surfaces of the first helical thread 110 (i.e., the first concave undercut surfaces 131 and the first convex undercut surfaces 141 in the fastener 100 of FIG. 1D) may not have mirror symmetry relative to each other about any plane perpendicular to the longitudinal axis 103 of the fastener 100. Rather, the first concave undercut surfaces 131 and the first convex undercut surfaces 141 may be generally parallel to each other. The same may be true for the second helical thread 120, in which the second concave undercut surfaces 132 and the second convex undercut surfaces 142 do not have mirror symmetry relative to each other, but may be generally parallel to each other.

Conversely, as also shown in FIG. 1D, the proximally-oriented surfaces of the first helical thread 110 may have mirror symmetry relative to the distally-oriented surfaces of the second helical thread 120. Specifically, the first concave undercut surfaces 131 may have mirror symmetry relative to the second convex undercut surfaces 142 about a plane 170 that bisects the space between them, and lies perpendicular to the longitudinal axis 103.

Similarly, the distally-oriented surfaces of the first helical thread 110 may have mirror symmetry relative to the proximally-oriented surfaces of the second helical thread 120. Specifically, the second concave undercut surfaces 132 may have mirror symmetry relative to the first convex undercut surfaces 141 about a plane 172 that bisects the space between them, and lies perpendicular to the longitudinal axis 103.

This mirror symmetry may be present along most of the length of the first helical thread 110 and the second helical thread 120, with symmetry across different planes arranged between adjacent turns of the first helical thread 110 and the second helical thread 120 along the length of the longitudinal axis 103. Such mirror symmetry may help more effectively capture bone between the first helical thread 110 and the second helical thread 120, and may also facilitate manufacture of the fastener 100, as will be described in more detail below.

Figure 10:
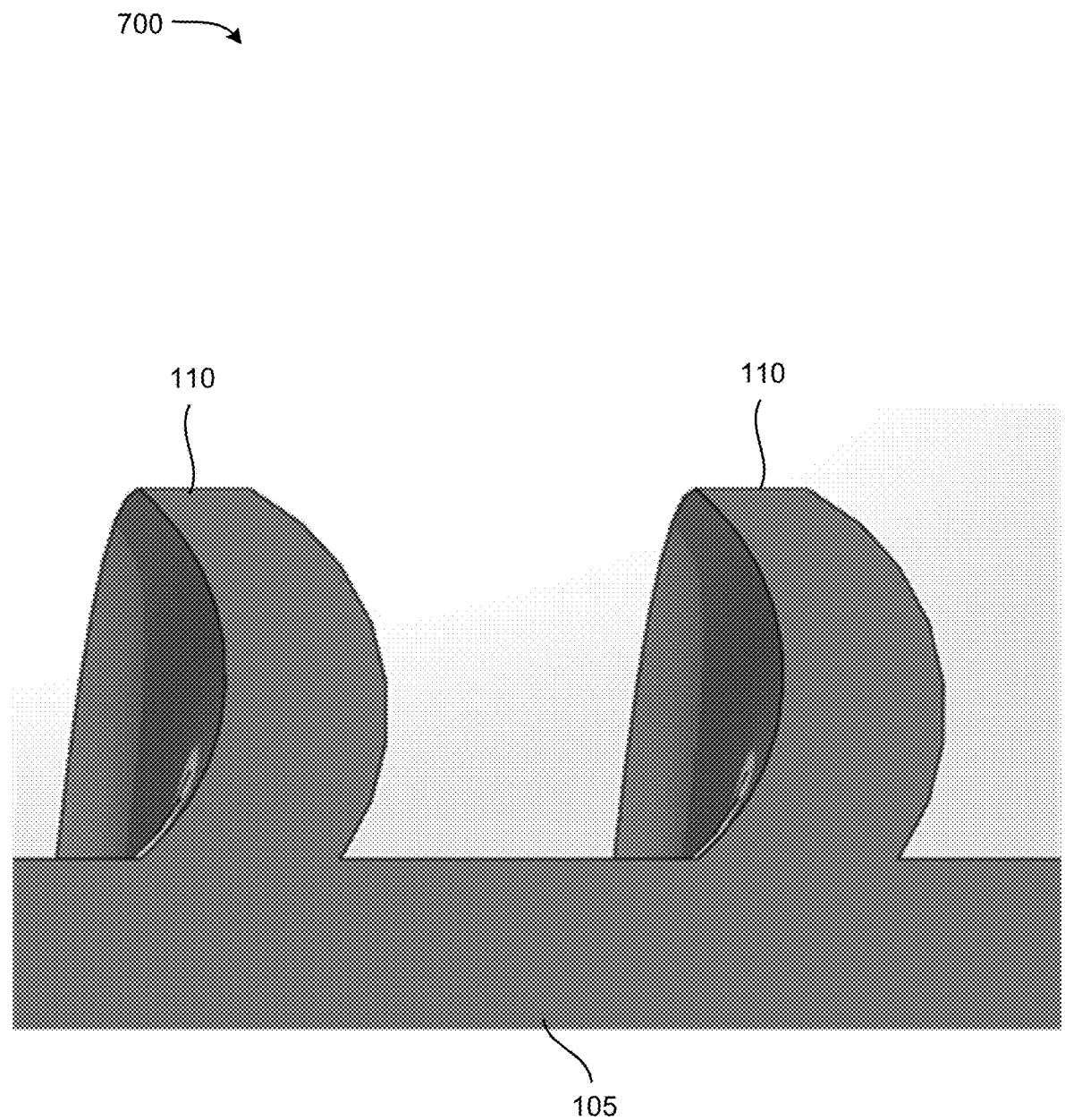
FIG. 10 illustrates a partial cross-sectional side view of a fastener comprising crescent-shaped threading.

In some embodiments, when the fastener 100 is viewed in section along a plane intersecting the longitudinal axis 103 of the shaft 105, the first helical thread 110 may include at least one partial crescent shape that is oriented toward (i.e., points toward) the distal end 102 of the shaft 105 and/or the proximal end 101 of the shaft 105. FIG. 10 illustrates a partial cross-sectional view of a fastener 700 comprising crescent shapes, as one non-limiting example of such an embodiment.

In some embodiments (not shown), when the fastener 100 is viewed in section along a plane intersecting the longitudinal axis 103 of the shaft 105, the first helical thread 110 may include at least one partial crescent shape that is oriented toward (i.e., points toward) the distal end 102 of the shaft 105, and the second helical thread 120 may include at least one partial crescent shape that is oriented toward (i.e., points toward) the proximal end 101 of the shaft 105.

In some embodiments (not shown), the first helical thread 110 may include a first plurality of partial crescent shapes that are oriented toward (i.e., point toward) the distal end 102 of the shaft 105, and the second helical thread 120 may include a second plurality of partial crescent shapes that are oriented toward (i.e., point toward) the proximal end 101 of the shaft 105.

In some embodiments (not shown), the first plurality of partial crescent shapes and the second plurality of partial crescent shapes may be arranged in alternating succession along the shaft 105 of the fastener 100.

In some embodiments, a fastener may have only standard threads or only inverted threads. The type of threads that are desired may depend on the type and/or magnitude of loads to be applied to the fastener. For example, a screw loaded axially away from the bone in which it is implanted may advantageously have a standard thread, while a screw loaded axially toward the bone in which it is implanted may advantageously have an inverted thread. A screw that may experience multi-axial loading and/or off-loading conditions may advantageously include at least one standard thread and at least one inverted thread in order to increase bone fixation and load sharing between a bone/fastener interface during multi-axial and off-loading conditions to reduce high bone strain and distribute multi-axial forces applied to the bone in a load-sharing, rather than load-bearing, configuration. Shear loads and/or bending moments may also be optimally resisted with any chosen combination of threading, threading morphology, and/or threading variations contemplated herein to optimally resist shear loads, bending moments, multi-axial loading, off-loading conditions, etc.

In some embodiments, fasteners with standard threads may be used in conjunction with fasteners with inverted threads in order to accommodate different loading patterns.

In some embodiments, a single fastener may have both standard and inverted threads, like the fastener 100. Such a combination of threads may help the fastener 100 remain in place with unknown and/or varying loading patterns.

In some embodiments, the geometry of the threading of a fastener (with standard and/or inverted threads) may be varied to suit the fastener for a particular loading scheme. For example, the number of threads, the number of thread starts, the pitch of the threading, the lead(s) of the threading, the shape(s) of the threading, any dimension(s) associated with the threading (e.g., any length(s)/width(s)/height(s) associated with the threading), the major diameter(s), the minor diameter(s), any angulation/angles associated with any surfaces of the threading, the "handedness" of the threading (e.g., right-handed vs. left-handed), etc., may be varied accordingly to suit any specific medium of installation, loading pattern, application, procedure, etc., that may be involved.

In some embodiments, the material(s) of any portion of a fastener described herein may include, but are not limited to metals (e.g., titanium, cobalt, stainless steel, etc.), metal alloys, plastics, polymers, PEEK, UHMWPE, composites, additive particles, textured surfaces, biologics, biomaterials, bone, etc.

In some embodiments, any of the fasteners described herein may include additional features such as: self-tapping features, locking features (e.g., locking threading formed on a portion of the fastener, such as threading located on or near a head of the fastener), cannulation, any style of fastener head (or no fastener head at all), any style of torque connection interface (or no torque connection interface at all), etc.

In some embodiments, a tap (not shown) may be utilized to pre-form threading herein in a bone according to any threading shape that is disclosed herein. In this manner, taps with any suitable shape may be utilized in conjunction with any fastener described or contemplated herein to match or substantially match the threading geometry of a given fastener.

In some embodiments, a minor diameter of the fastener may be selected to match, or substantially match, a diameter of a pilot hole that is formed in a bone to avoid bone blowout when the fastener is inserted into the pilot hole.

Additionally or alternatively, the type of threads and/or thread geometry may be varied based on the type of bone in which the fastener is to be anchored. For example, fasteners anchored in osteoporotic bone may fare better with standard or inverted threads, or when the pitch, major diameter, and/or minor diameter are increased or decreased, or when the angulation of thread surfaces is adjusted, etc.

In some embodiments, a surgical kit may include multiple fasteners with any of the different thread options described or contemplated herein. The surgeon may select the appropriate fastener(s) from the kit based on the particular loads to be applied and/or the quality of bone in which the fastener(s) are to be anchored.

Continuing with FIG. 1D, in some embodiments the first helical thread 110 may include a plurality of first undercut surfaces 111, a plurality of second undercut surfaces 112, a plurality of third undercut surfaces 113, and a plurality of fourth open surfaces 114.

In some embodiments, the second helical thread 120 may include a plurality of fifth undercut surfaces 125, a plurality of sixth undercut surfaces 126, a plurality of seventh undercut surfaces 127, and a plurality of eighth open surfaces 128.

In some embodiments one or more of the plurality of first undercut surfaces 111, the plurality of second undercut surfaces 112, the plurality of third undercut surfaces 113, the plurality of fourth open surfaces 114, the plurality of fifth undercut surfaces 125, the plurality of sixth undercut surfaces 126, the plurality of seventh undercut surfaces 127, and the plurality of eighth open surfaces 128 may comprise at least one flat or substantially flat surface.

In some embodiments, the plurality of first undercut surfaces 111, the plurality of third undercut surfaces 113, the plurality of sixth undercut surfaces 126, and the plurality of eighth open surfaces 128 may be angled towards the distal end 102 of the shaft 105.

In some embodiments, the plurality of second undercut surfaces 112, the plurality of fourth open surfaces 114, the plurality of fifth undercut surfaces 125, and the plurality of seventh undercut surfaces 127 may be angled towards the proximal end 101 of the shaft 105.

In some embodiments, when the fastener 100 is viewed in section along a plane that intersects the longitudinal axis 103 of the shaft 105 (as shown in FIG. 1D), the first helical thread 110 may include at least one chevron shape that is oriented toward (i.e., points toward) the distal end 102 of the shaft 105. Likewise, the second helical thread 120 may also include at least one chevron shape that is oriented toward (i.e., points toward) the proximal end 101 of the shaft 105.

In some embodiments, when the fastener 100 is viewed in section along a plane that intersects the longitudinal axis 103 of the shaft 105 (as shown in FIG. 1D), the first helical thread 110 may include a first plurality of chevron shapes that are oriented toward (i.e., point toward) the distal end 102 of the shaft 105. Likewise, the second helical thread 120 may include a second plurality of chevron shapes that are oriented toward (i.e., point toward) the proximal end 101 of the shaft 105.

In some embodiments, the first plurality of chevron shapes and the second plurality of chevron shapes may be arranged in alternating succession along the shaft 105 of the fastener 100, (e.g., see FIG. 1D).

In some embodiments, a plurality of first interlocking spaces 161 and a plurality of second interlocking spaces 162 may be formed between the first helical thread 110 and the second helical thread 120 along the shaft 105 of the fastener 100.

In some embodiments, the plurality of first interlocking spaces 161 may be formed intermediate the first concave undercut surfaces 131 and the second concave undercut surfaces 132.

In some embodiments, the plurality of second interlocking spaces 162 may be formed intermediate the first convex undercut surfaces 141 and the second convex undercut surfaces 142.

In some embodiments, the plurality of first interlocking spaces 161 may be larger in size than the plurality of second interlocking spaces.

In some embodiments, the plurality of first interlocking spaces 161 and the plurality of second interlocking spaces 162 may be shaped and/or configured to interlock with bone/other tissues received therein to increase fixation of the fastener 100 within the bone/other tissues and provide additional resistance against multi-axial forces that may be applied to the fastener 100 and/or the bone/other tissues.

In some embodiments, the plurality of second undercut surfaces 112 and the plurality of sixth undercut surfaces 126 may be angled toward each other to trap bone/other tissues within the plurality of first interlocking spaces 161 in order to increase fixation and resistance against multi-axial forces.

In some embodiments, the plurality of third undercut surfaces 113 and the plurality of seventh undercut surfaces 127 may be angled toward each other to trap bone/other tissues within the plurality of second interlocking spaces 162 in order to increase fixation and resistance against multi-axial forces.

In some embodiments, the plurality of first undercut surfaces 111 and the plurality of fifth undercut surfaces 125 may each form an angle α with respect to the longitudinal axis 103 of the shaft 105, as shown in FIG. 1D.

In some embodiments, the angle α may be greater than 90 degrees.

In some embodiments, the plurality of second undercut surfaces 112 and the plurality of sixth undercut surfaces 126 may each form an angle β with respect to the longitudinal axis 103 of the shaft 105.

In some embodiments, the angle β may be less than 90 degrees.

In some embodiments, the plurality of third undercut surfaces 113 and the plurality of seventh undercut surfaces 127 may each form an angle θ with respect to the longitudinal axis 103 of the shaft 105.

In some embodiments, the angle θ may be approximately 90 degrees.

In some embodiments, the angle θ may be greater than 90 degrees.

Figure 2A:
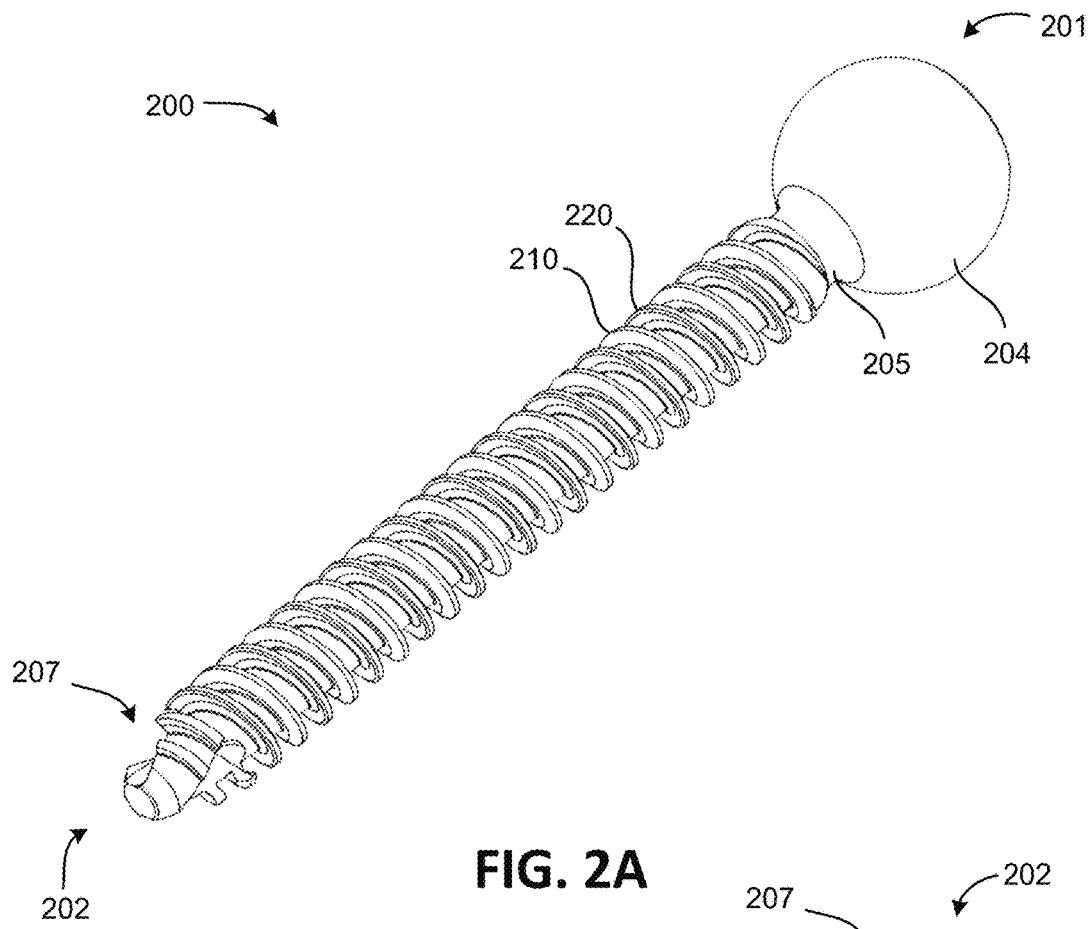
FIG. 2A illustrates a front perspective view of a fastener, according to another embodiment of the present disclosure.
Figure 2B:
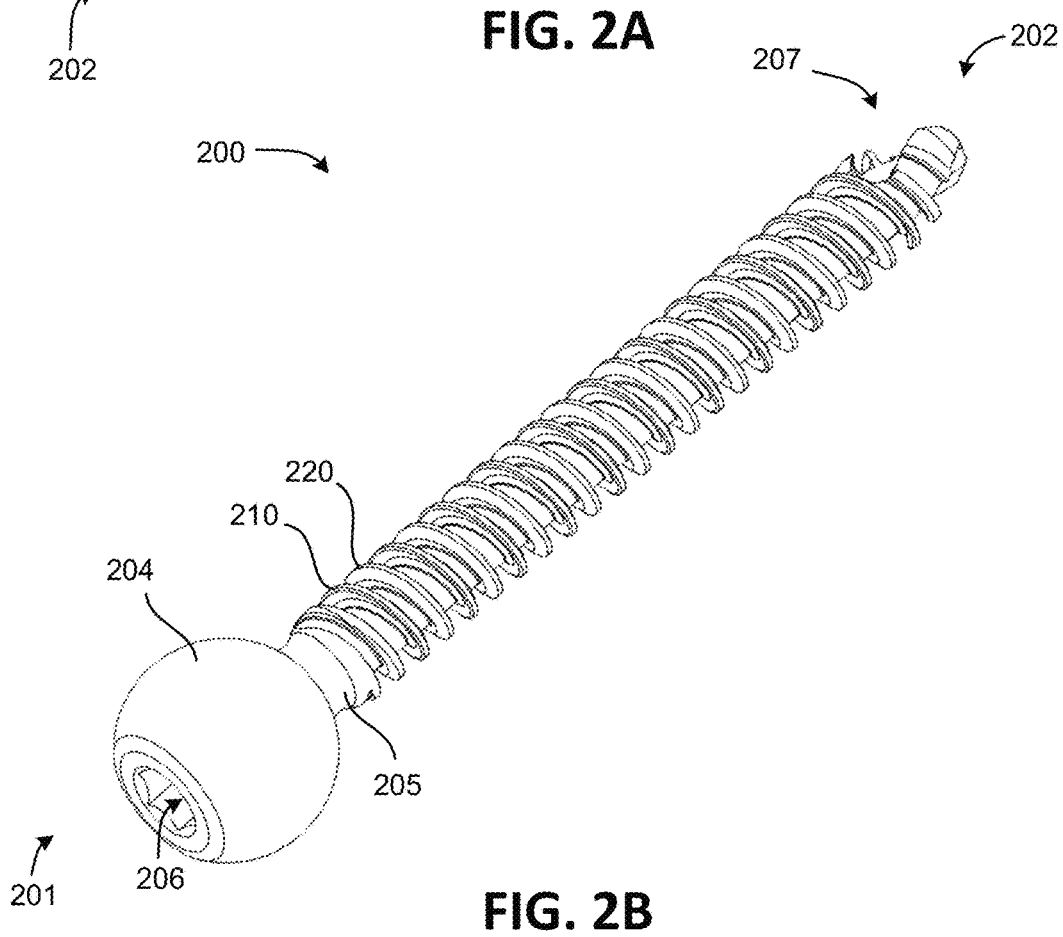
FIG. 2B illustrates a rear perspective view of the fastener of FIG. 2A.
Figure 2C:
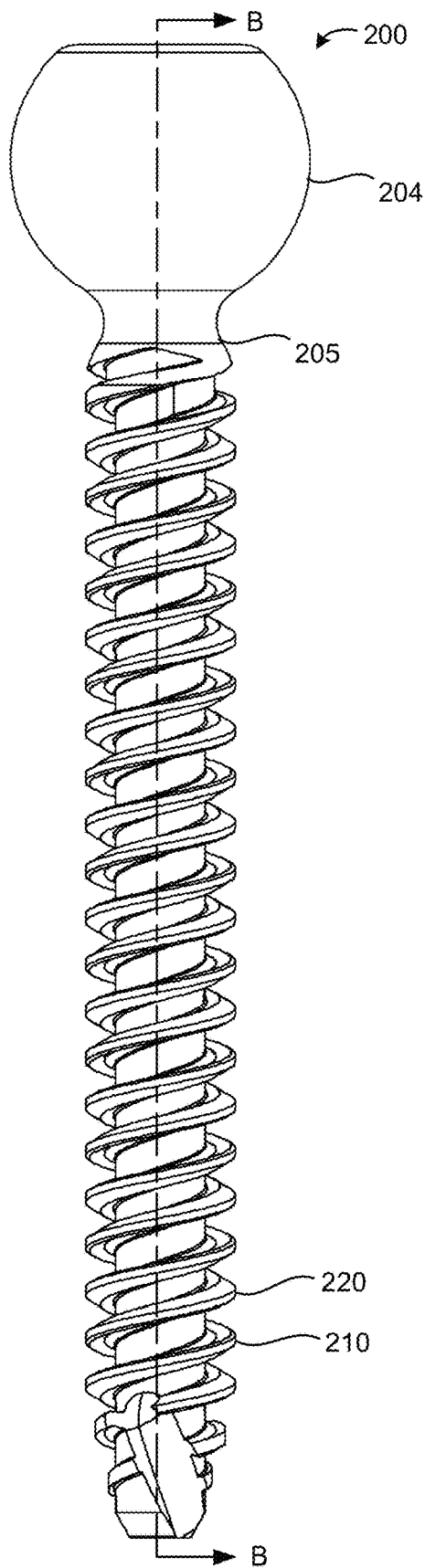
FIG. 2C illustrates a side view of the fastener of FIG. 2A.
Figure 2D:
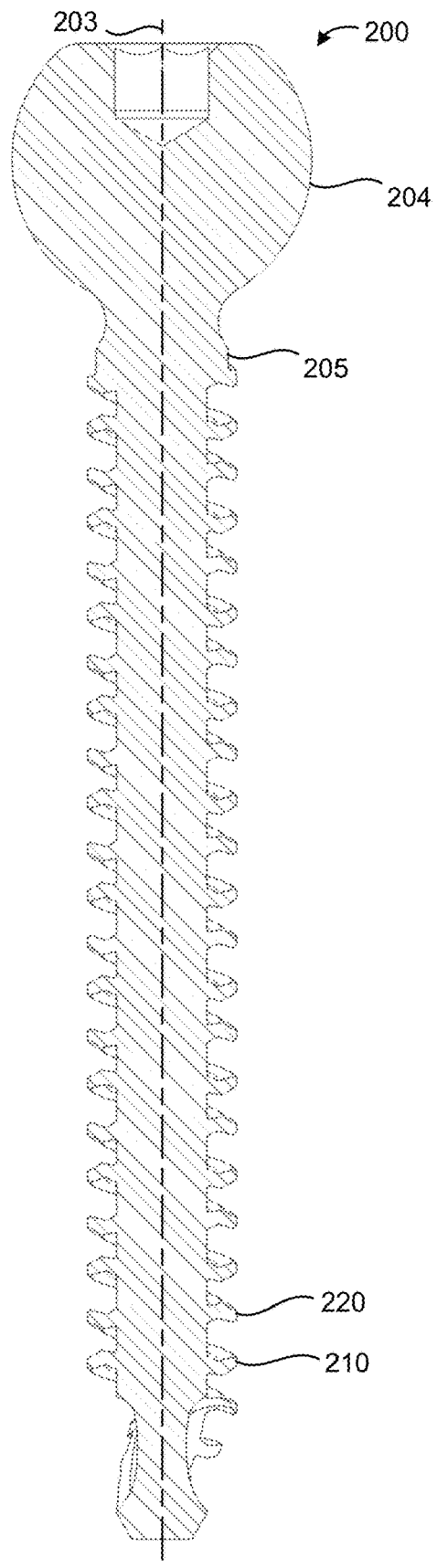
FIG. 2D illustrates a cross-sectional side view of the fastener of FIG. 2A taken along the line B-B shown in FIG. 2C.

FIGS. 2A-D illustrate various views of a polyaxial screw or fastener 200, according to another embodiment of the present disclosure. Specifically, FIG. 2A is a front perspective view of the fastener 200, FIG. 2B is a rear perspective view of the fastener 200, FIG. 2C is a side view of the fastener 200, and FIG. 2D is a cross-sectional side view of the fastener 200 taken along the line B-B in FIG. 2C. The fastener 200 may include a shaft 205 having a proximal end 201, a distal end 202, and a longitudinal axis 203. The fastener 200 may also include a polyaxial head 204 located at the proximal end 201 of the shaft 205, a torque connection interface 206 formed in/on the polyaxial head 204, and a self-tapping feature 207 formed in the distal end 202 of the shaft 205. In some embodiments, the fastener 200 may include a first helical thread 210 disposed about the shaft 205, and a second helical thread 220 disposed about the shaft 205 adjacent the first helical thread 210. In these embodiments, the fastener 200 may comprise a "dual start" or "dual lead" thread configuration. However, it will also be understood that the fastener 200 may include any thread configuration, feature, or morphology described or contemplated herein to achieve optimal fixation within a given bone/tissue.

Figure 3A:
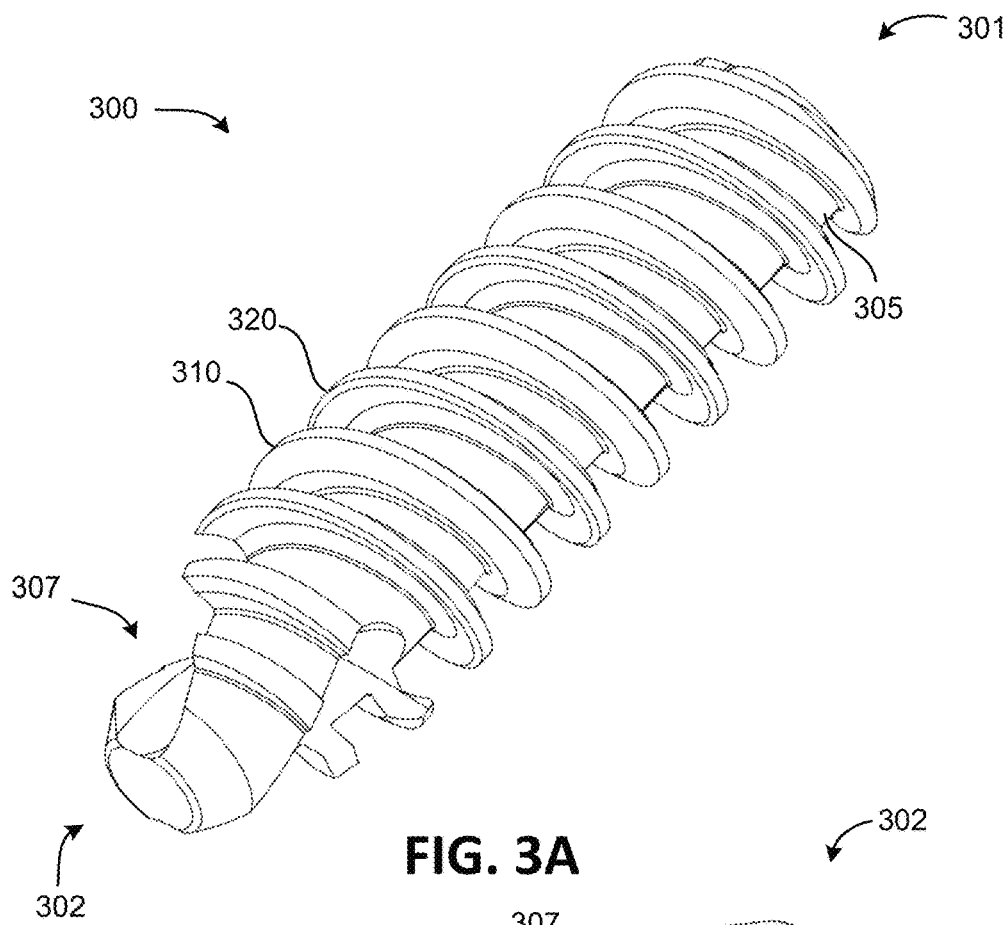
FIG. 3A illustrates a front perspective view of a fastener, according to another embodiment of the present disclosure.
Figure 3B:
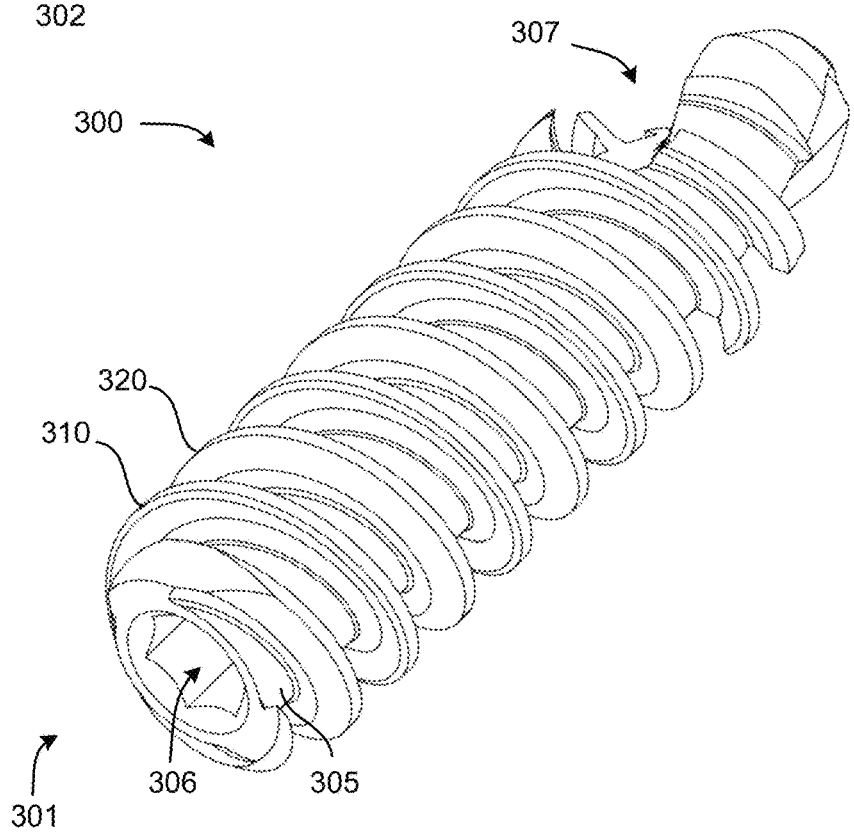
FIG. 3B illustrates a rear perspective view of the fastener of FIG. 3A.
Figure 3C:
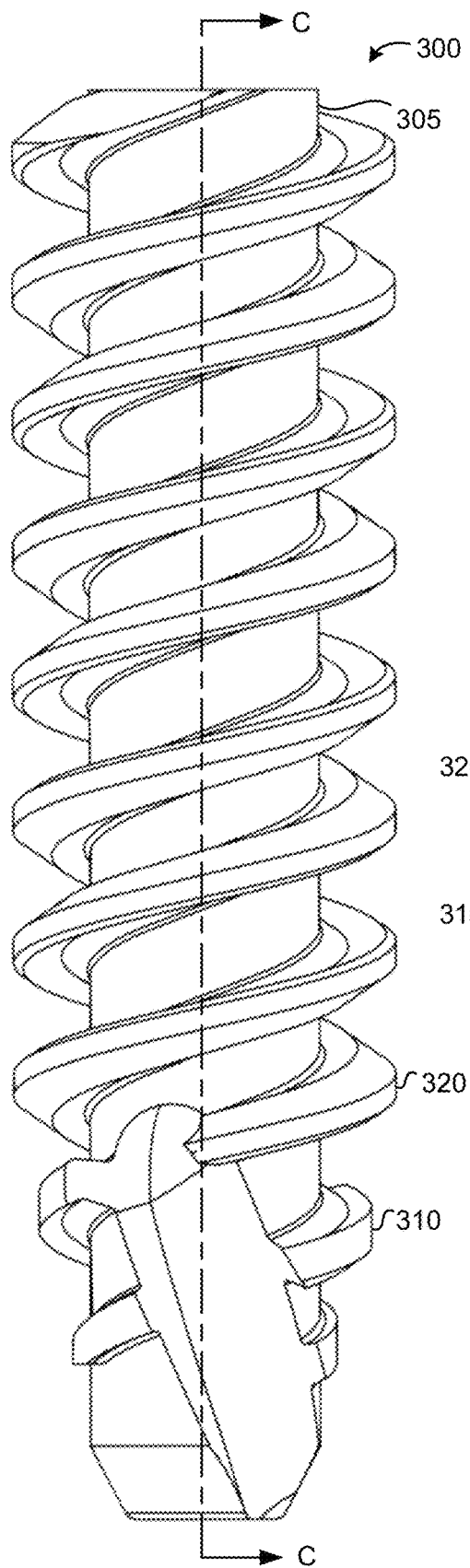
FIG. 3C illustrates a side view of the fastener of FIG. 3A.
Figure 3D:
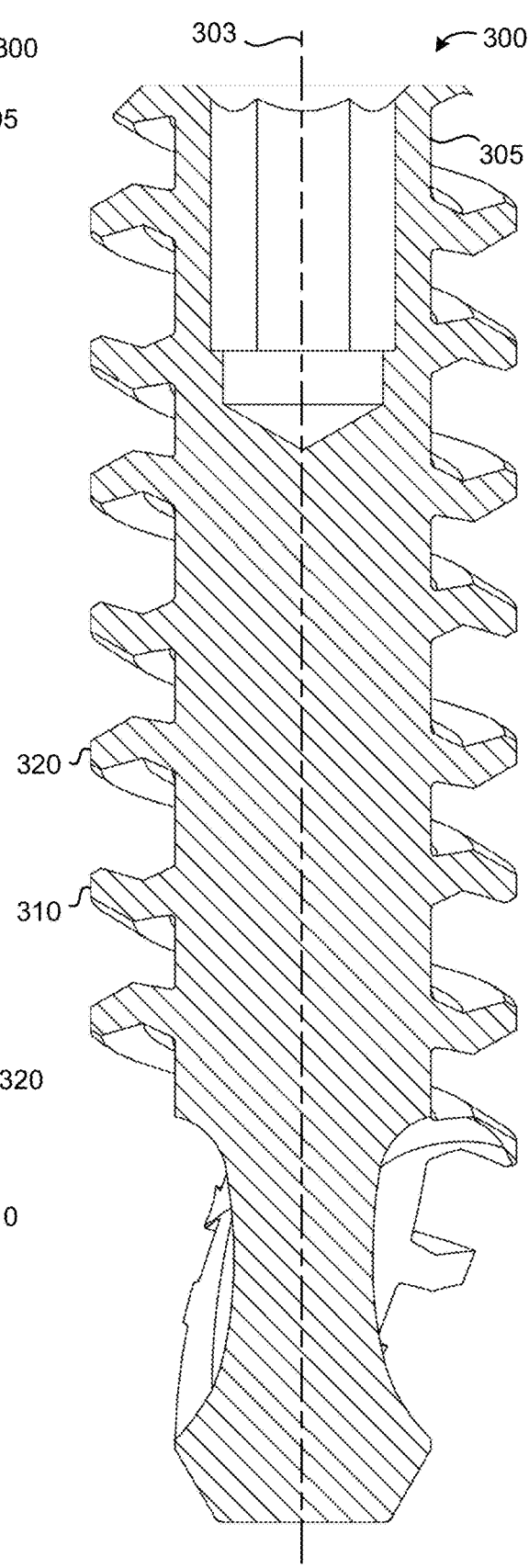
FIG. 3D illustrates a cross-sectional side view of the fastener of FIG. 3A taken along the line C-C shown in FIG. 3C.

FIGS. 3A-D illustrate various views of a headless screw or fastener 300, according to another embodiment of the present disclosure. Specifically, FIG. 3A is a front perspective view of the fastener 300, FIG. 3B is a rear perspective view of the fastener 300, FIG. 3C is a side view of the fastener 300, and FIG. 3D is a cross-sectional side view of the fastener 300 taken along the line C-C in FIG. 3C. The fastener 300 may include a shaft 305 having a proximal end 301, a distal end 302, and a longitudinal axis 303. The fastener 300 may also include a torque connection interface 306 formed in the proximal end 301 of the shaft 305 and a self-tapping feature 307 formed in the distal end 302 of the shaft 305. In some embodiments, the fastener 300 may include a first helical thread 310 disposed about the shaft 305, and a second helical thread 320 disposed about the shaft 305 adjacent the first helical thread 310. In these embodiments, the fastener 300 may comprise a "dual start" or "dual lead" thread design with alternating standard and inverted threads. However, it will also be understood that the fastener 300 may include any thread configuration, feature, or morphology described or contemplated herein to achieve optimal fixation within a given bone/tissue.

Figure 4A:
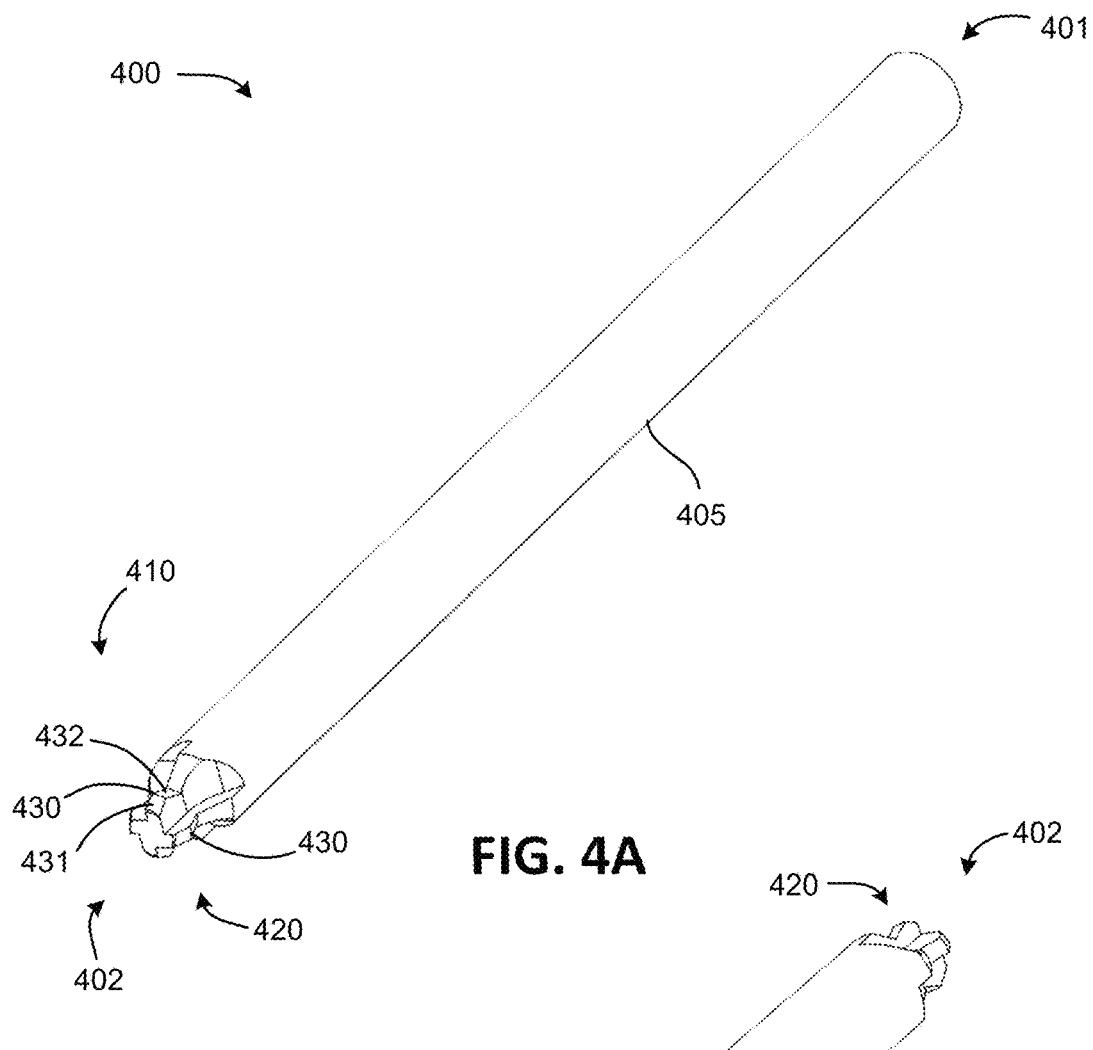
FIG. 4A illustrates a front perspective view of a mill tool, according to one embodiment of the present disclosure.
Figure 4B:
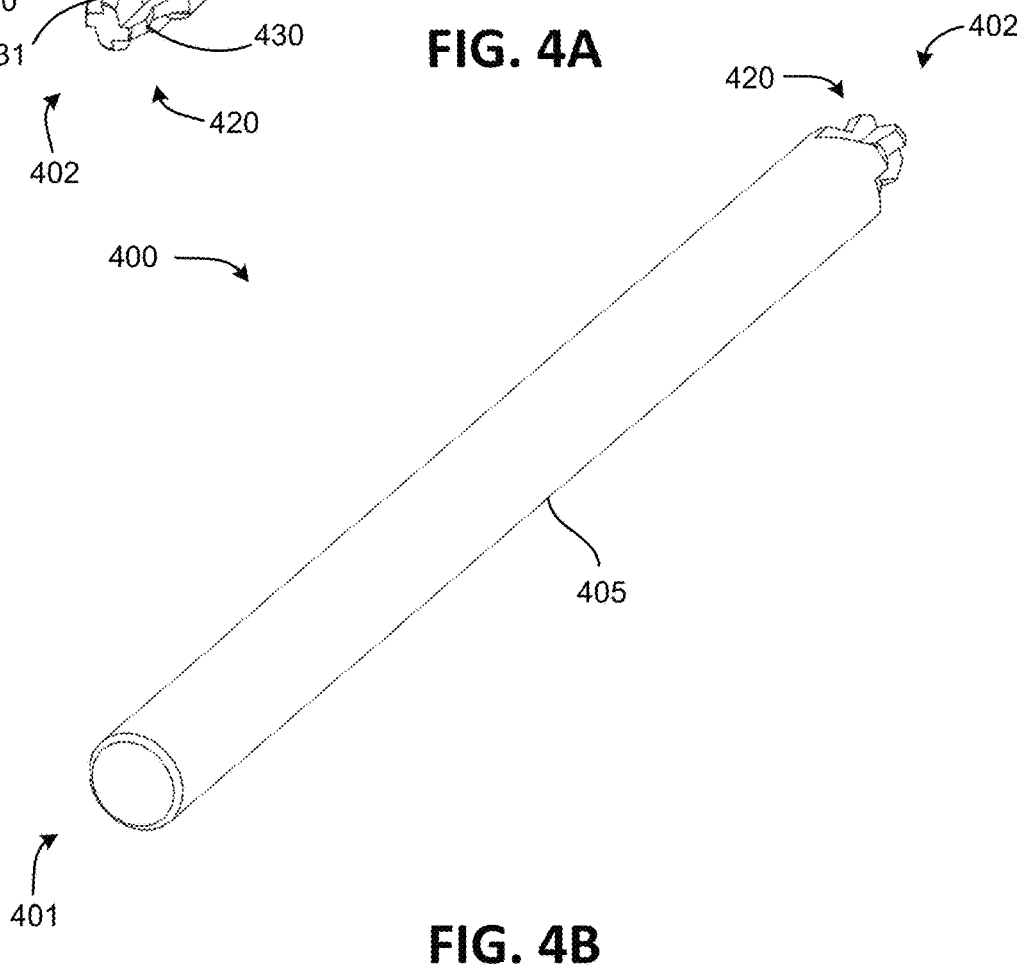
FIG. 4B illustrates a rear perspective view of the mill tool of FIG. 4A.
Figures 4C, 4D:
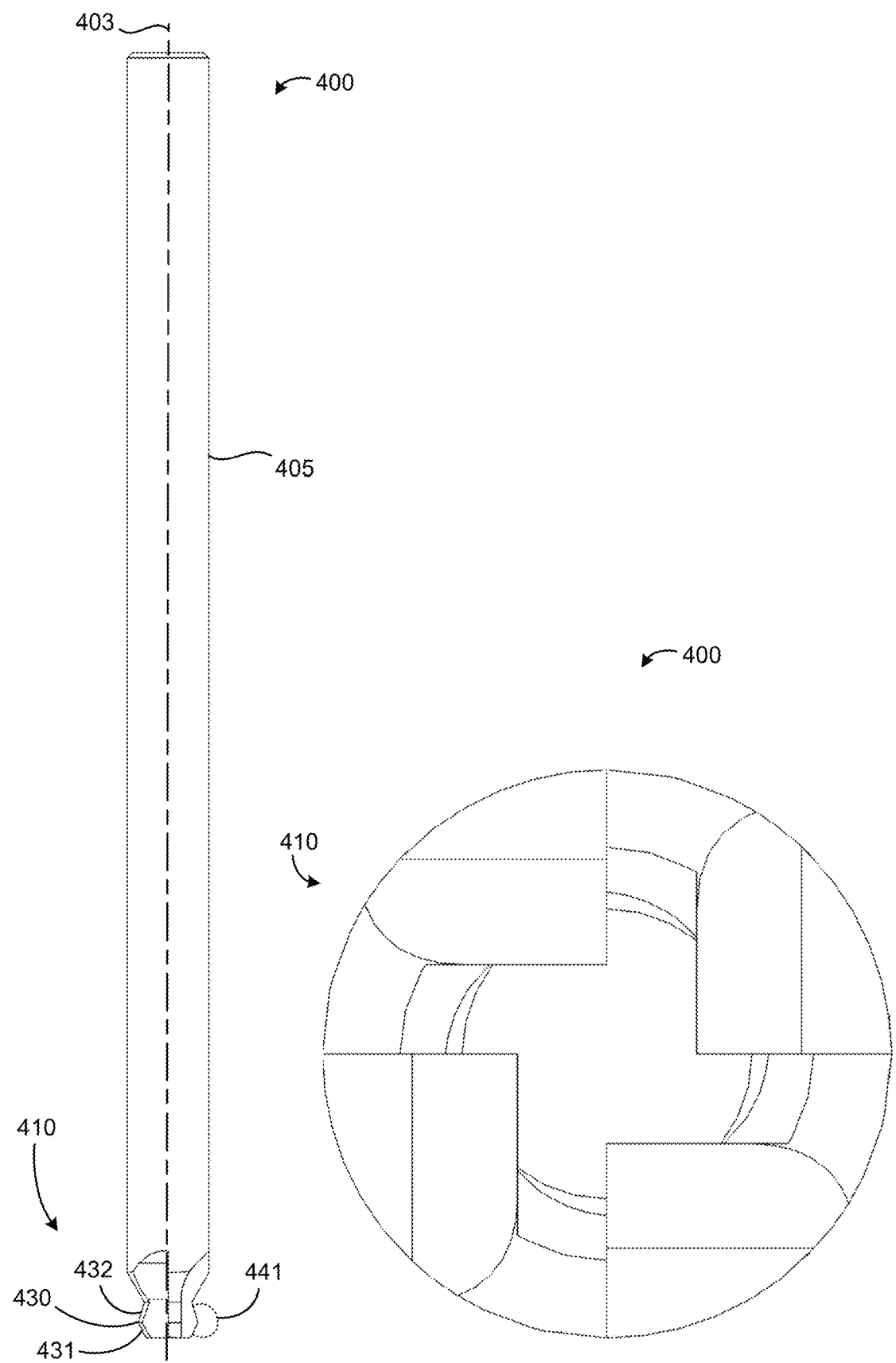
FIG. 4C illustrates a side view of the mill tool of FIG. 4A.
FIG. 4D illustrates a front view of the mill tool of FIG. 4A.

FIGS. 4A-D illustrate various views of a first mill tool 400, according to one embodiment of the present disclosure. Specifically, FIG. 4A is a front perspective view of the first mill tool 400, FIG. 4B is a rear perspective view of the first mill tool 400, FIG. 4C is a side view of the first mill tool 400, and FIG. 4D is a front view of the first mill tool of FIG. 400. The first mill tool 400 may include a shaft 405 having a proximal end 401, a distal end 402, and a longitudinal axis 403.

In some embodiments, the first mill tool 400 may include a first cutting head 410 comprising one or more first cutting blades 420 disposed at the distal end 402 of the shaft 405.

In some embodiments, the one or more first cutting blades 420 may comprise at least one convex cutting surface 430.

In some embodiments, the at least one convex cutting surface 430 may comprise a first facet 431 and a second facet 432 (e.g., see FIGS. 4A and 4C, as one non-limiting example).

In some embodiments, the first facet 431 and/or the second facet 432 may comprise one or more flat surfaces.

In some embodiments, the first facet 431 and/or the second facet 432 may comprise one or more curved surfaces.

In some embodiments, the first facet 431 and the second facet 432 may be angled with respect to each other to form the at least one convex cutting surface 430.

In some embodiments, the first facet 431 and the second facet 432 may be angled with respect to each other by a first angle 441 that may be greater than 180 degrees to form the at least one convex cutting surface 430.

Figure 5A:
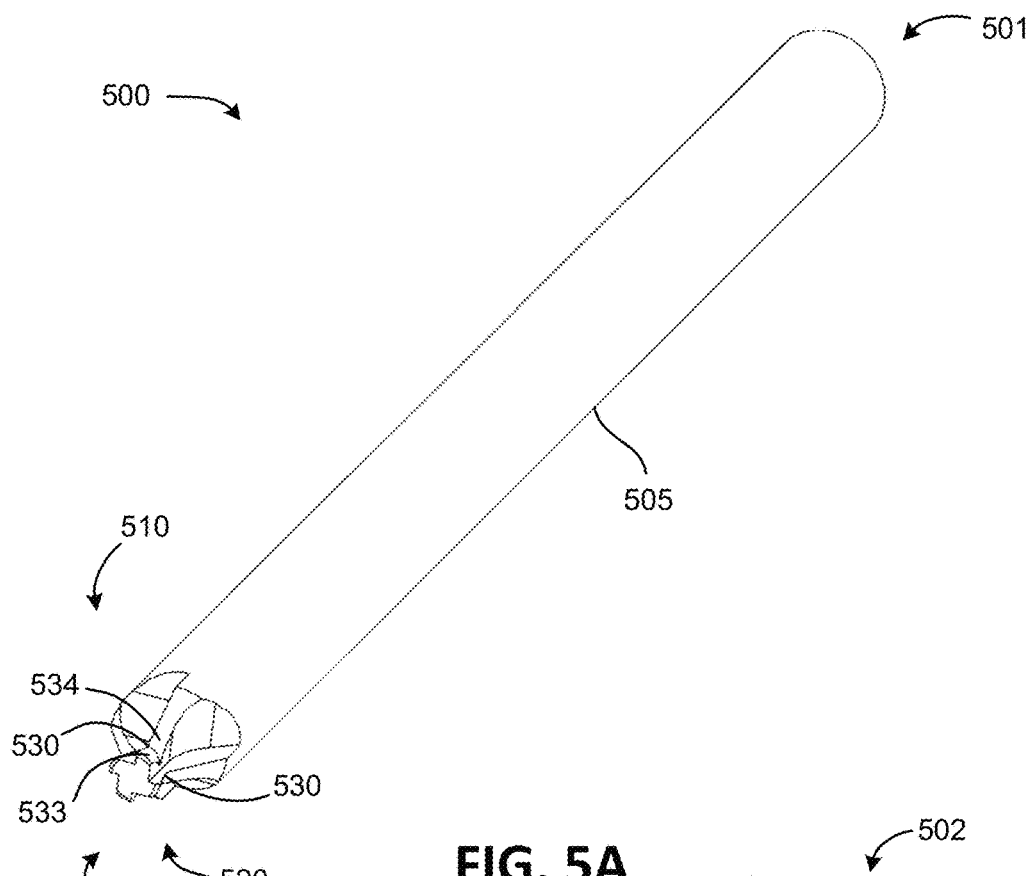
FIG. 5A illustrates a front perspective view of a mill tool, according to another embodiment of the present disclosure.
Figure 5B:
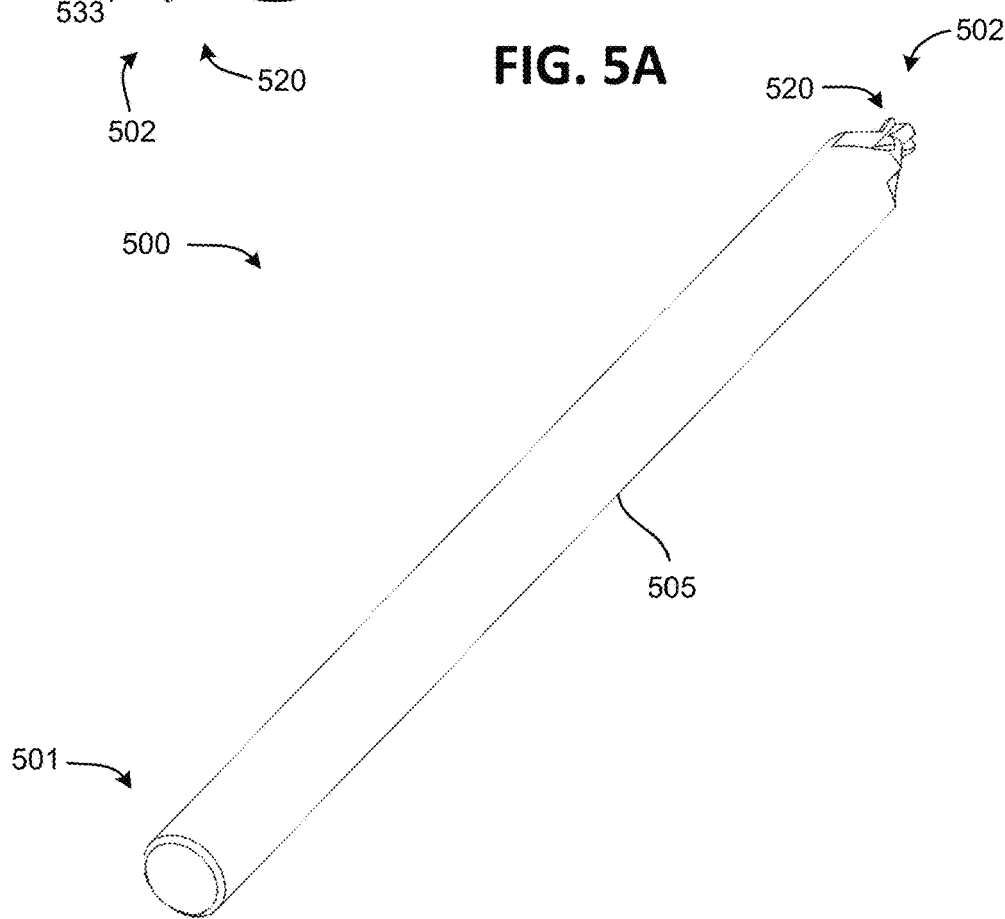
FIG. 5B illustrates a rear perspective view of the mill tool of FIG. 5A.
Figure 5C:
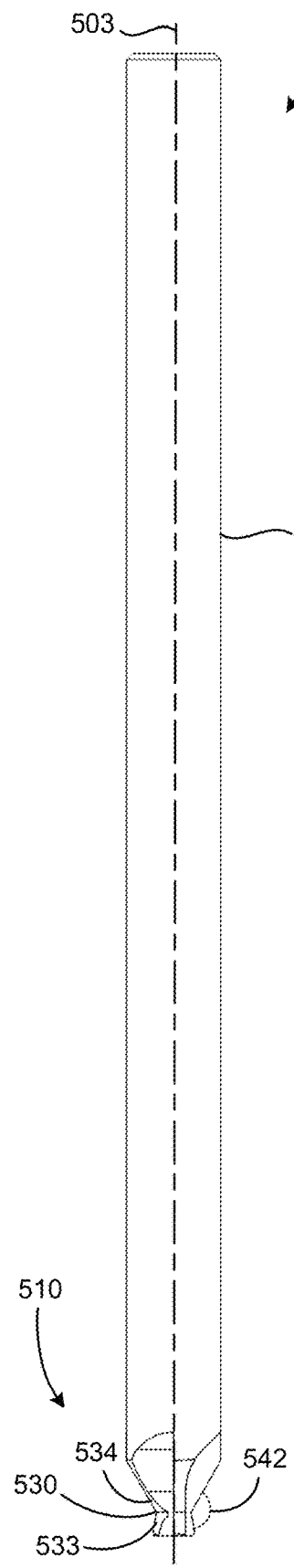
FIG. 5C illustrates a side view of the mill tool of FIG. 5A.
Figure 5D:
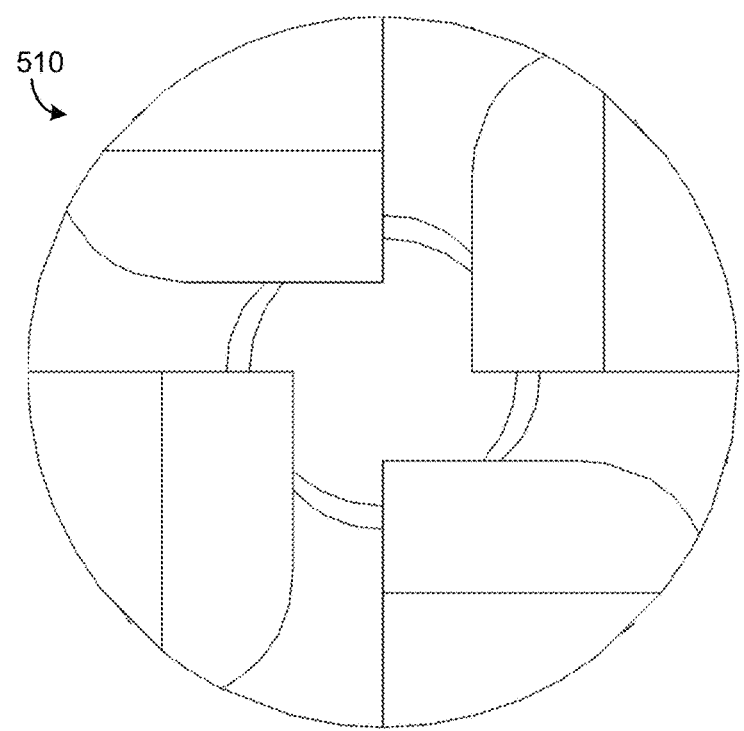
FIG. 5D illustrates a front view of the mill tool of FIG. 5A.

FIGS. 5A-D illustrate various views of a second mill tool 500, according to another embodiment of the present disclosure. Specifically, FIG. 5A is a front perspective view of the second mill tool 500, FIG. 5B is a rear perspective view of the second mill tool 500, FIG. 5C is a side view of the second mill tool 500, and FIG. 5D is a front view of the second mill tool of FIG. 500. The second mill tool 500 may include a shaft 505 having a proximal end 501, a distal end 502, and a longitudinal axis 503.

In some embodiments, the second mill tool 500 may include a second cutting head 510 comprising one or more second cutting blades 520 disposed at the distal end 502 of the shaft 505.

In some embodiments, the one or more second cutting blades 520 may comprise at least one concave cutting surface 530.

In some embodiments, the at least one concave cutting surface 530 may comprise a third facet 533 and a fourth facet 534 (e.g., see FIGS. 5A and 5C, as one non-limiting example).

In some embodiments, the third facet 533 and/or the fourth facet 534 may comprise one or more flat surfaces.

In some embodiments, the third facet 533 and/or the fourth facet 534 may comprise one or more curved surfaces.

In some embodiments, the third facet 533 and the fourth facet 534 may be angled with respect to each other to form the at least one concave cutting surface 530.

In some embodiments, the third facet 533 and the fourth facet 534 may be angled with respect to each other by a second angle 542 that may be less than 180 degrees to form the at least one concave cutting surface 530.

Figure 6:
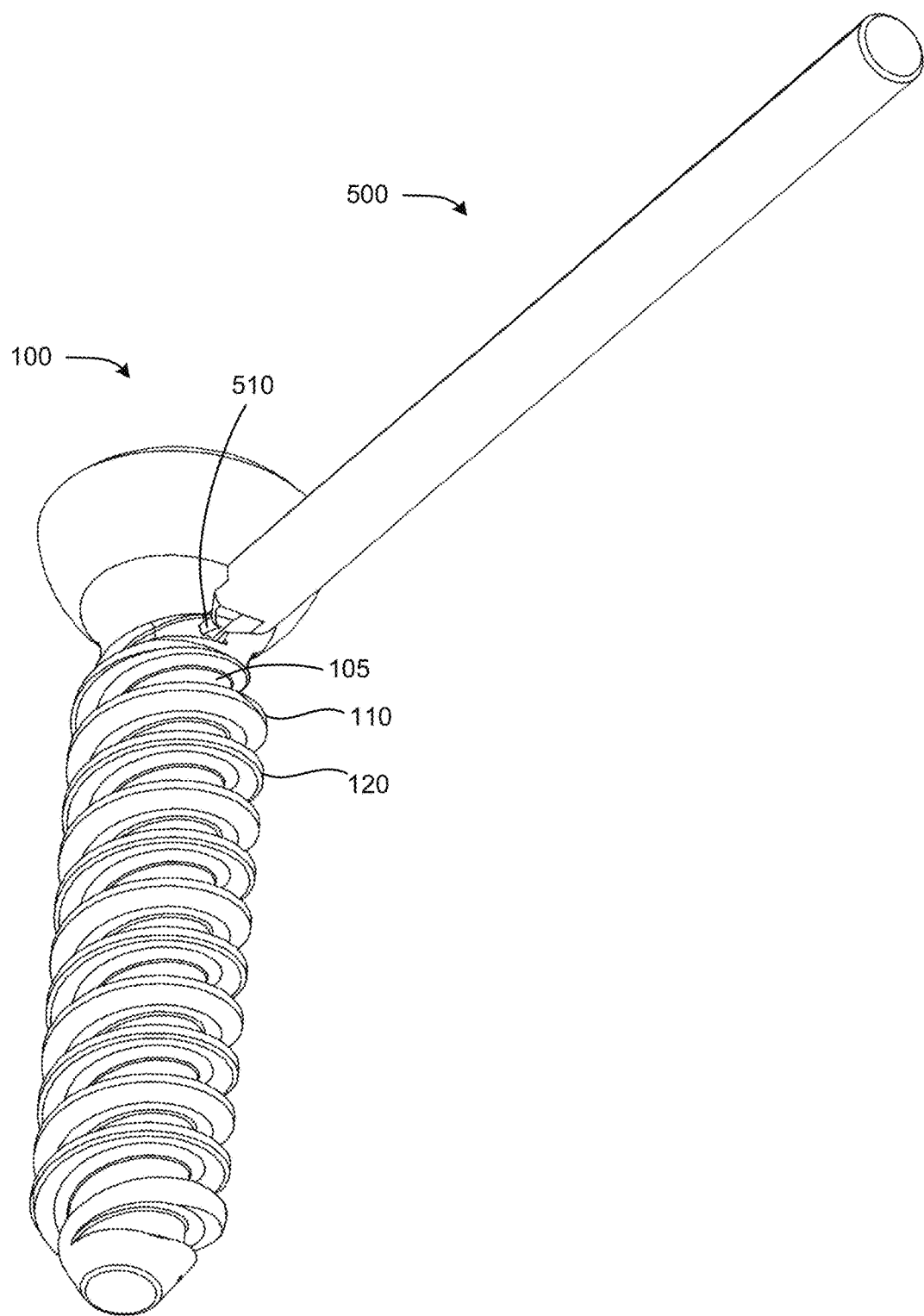
FIG. 6 illustrates a perspective view of the mill tool of FIG. 5A performing a milling operation on the fastener of FIG. 1A.
Figure 7:
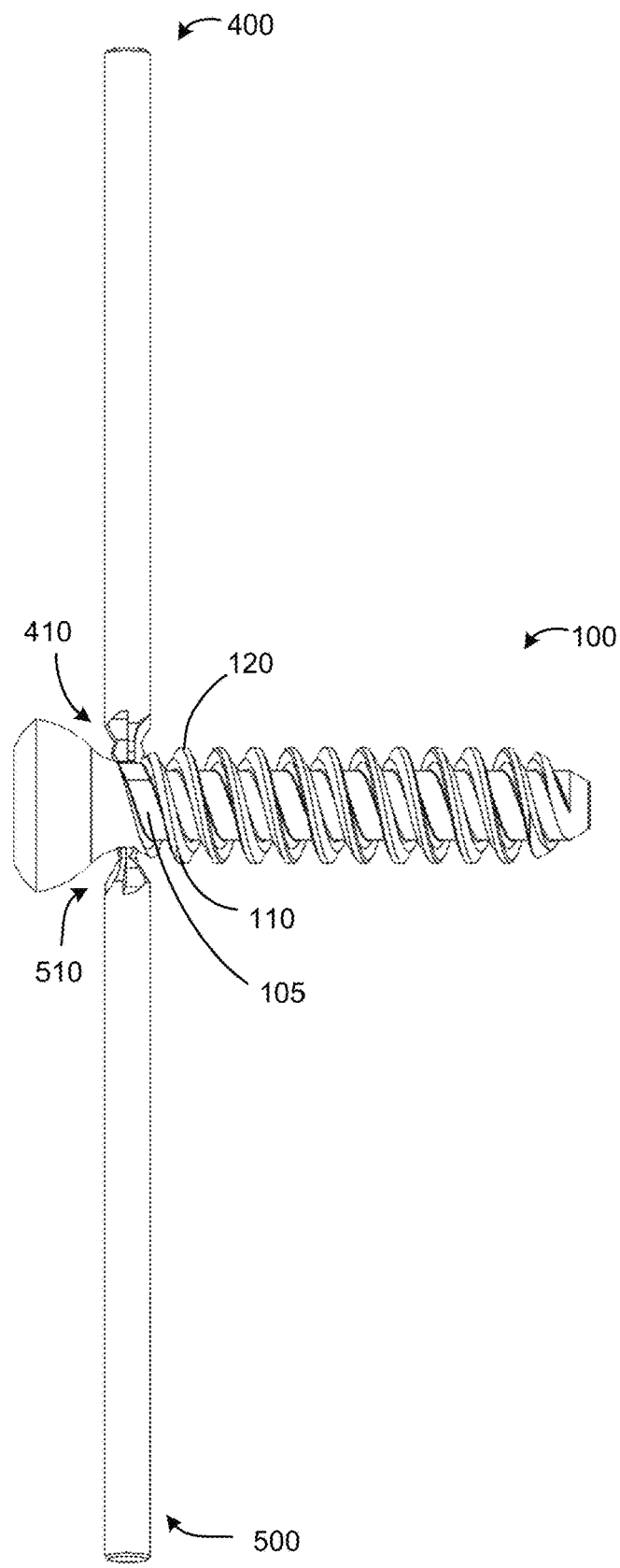
FIG. 7 illustrates a side view of the mill tool of FIG. 5A and the mill tool of FIG. 4A performing milling operations on the fastener of FIG. 1A.
Figure 8:
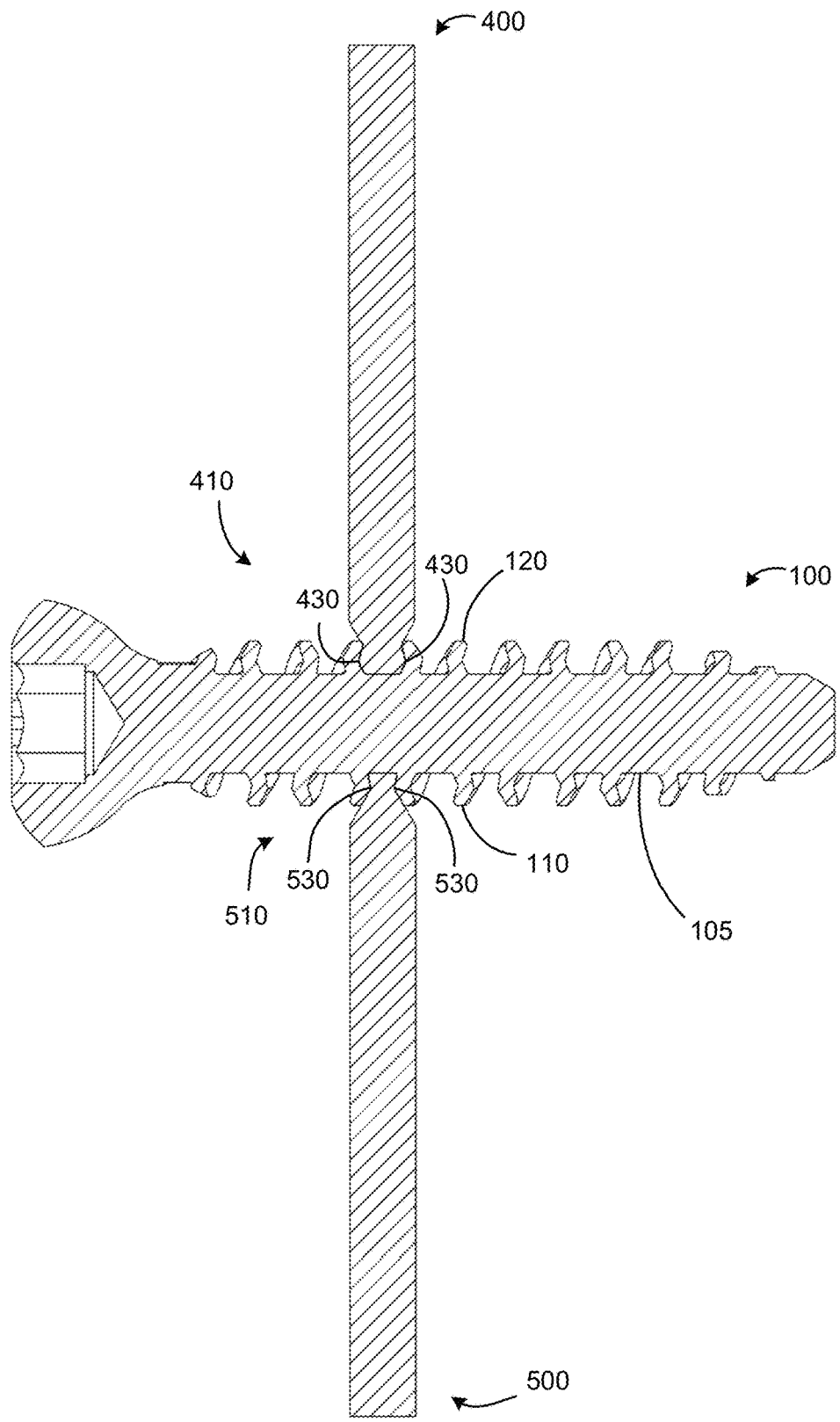
FIG. 8 illustrates a cross-sectional side view of the mill tool of FIG. 5A and the mill tool of FIG. 4A performing milling operations on the fastener of FIG. 1A.

FIGS. 6-8 illustrate various views of the first mill tool 400 and the second mill tool 500 performing milling operations on the fastener 100 of FIG. 1A to form the first helical thread 110 and the second helical thread 120. Specifically, FIG. 6 is a perspective view of the second mill tool 500 performing a milling operation on the fastener 100, FIG. 7 is a side view of both the first mill tool 400 and the second mill tool 500 performing milling operations on the fastener 100 simultaneously, and FIG. 8 is a cross-sectional side view of both the first mill tool 400 and the second mill tool 500 performing milling operations on the fastener 100 simultaneously. FIG. 8 illustrates how the first mill tool 400 and the second mill tool 500 may be utilized to form the plurality of first interlocking spaces 161 and the plurality of second interlocking spaces 162 between the first helical thread 110 and the second helical thread 120. Various milling techniques that may be utilized to form the helical threading described herein will now be described in more detail with reference to FIG. 9.

Figure 9:
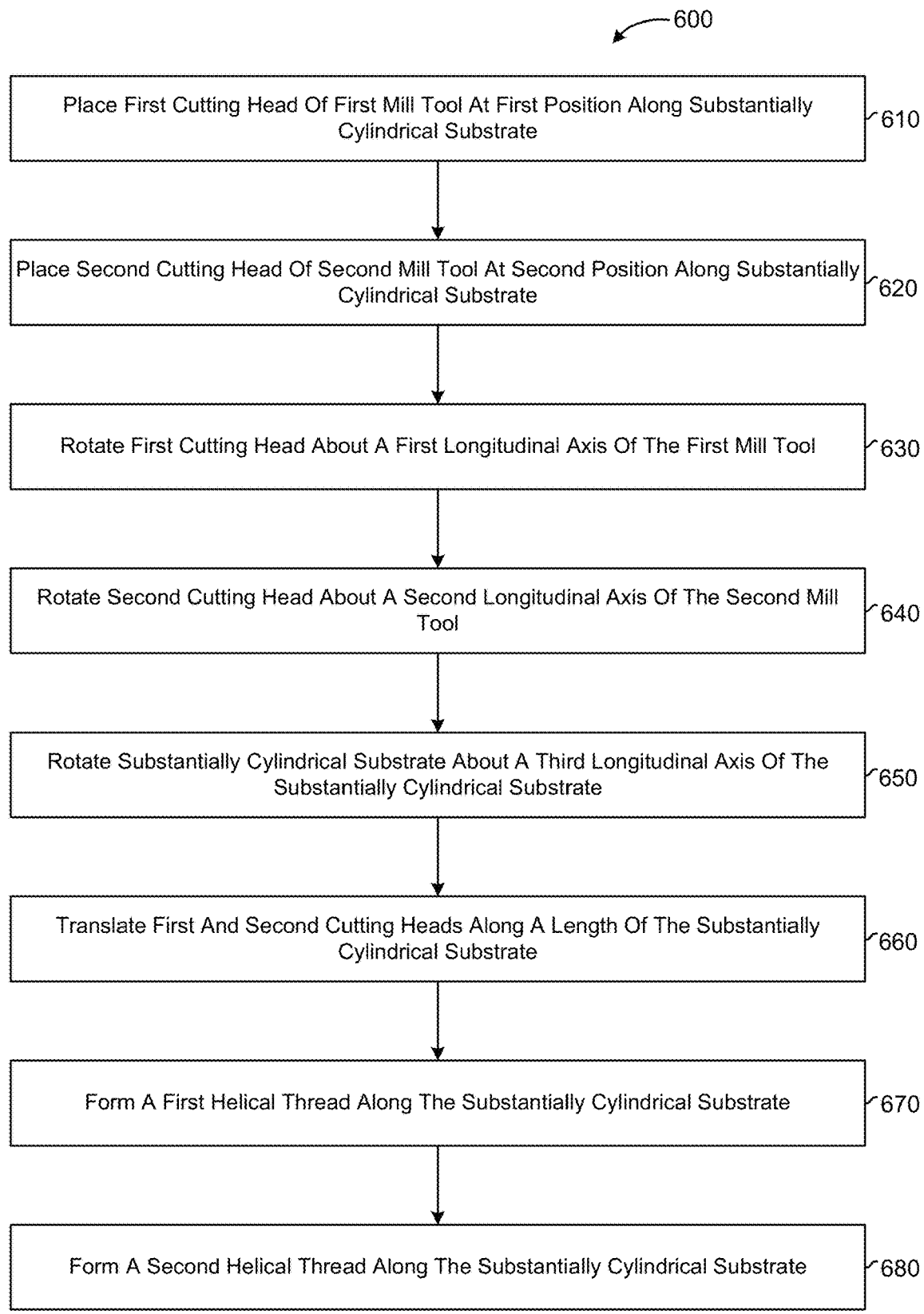
FIG. 9 illustrates a flow diagram of a process for forming threading on a fastener, according to one embodiment of the present disclosure.

FIG. 9 illustrates a flow diagram of a process or method 600 of forming threading on a shaft or a substantially cylindrical substrate (not shown) to create a threaded fastener or implantable bone anchor, according to some embodiments of the present disclosure.

In some embodiments, the method 600 may begin with a step 610 in which a first cutting head of a first mill tool may be placed at a first position along the substantially cylindrical substrate.

In some embodiments of the method 600, a second cutting head of a second mill tool may, alternatively, or in addition thereto, be placed at a second position along the substantially cylindrical substrate in a step 620 at the same time (or at a different time) as the first cutting head is placed at the first position. However, it will also be understood that, in some embodiments, any number of cutting heads/mill tools may be utilized to form any number of helical threads (as previously discussed) about the substantially cylindrical substrate, in either a successive or a simultaneous manner.

In some embodiments, the first cutting head may be placed adjacent the second cutting head along a side of the substantially cylindrical substrate.

In some embodiments, the first longitudinal axis of the first mill tool may be placed substantially parallel to the second longitudinal axis of the second mill tool.

In some embodiments, the first cutting head may be spaced apart from the second cutting head along the substantially cylindrical substrate.

In some embodiments, the first cutting head may be placed opposite the second cutting head along opposing sides of the substantially cylindrical substrate.

In some embodiments, the first cutting head may be placed on a first side of the substantially cylindrical substrate and the second cutting head may be placed on a second side of the substantially cylindrical substrate.

In some embodiments, the first cutting head may be separated from the second cutting head by any selected degree of rotation about the third longitudinal axis of the substantially cylindrical substrate.

In some embodiments, the first cutting head and the second cutting head may be placed on opposing sides of the substantially cylindrical substrate and/or may be separated from each other by about 180 degrees of rotation with respect to the third longitudinal axis of the substantially cylindrical substrate.

Once the first mill tool and/or the second mill tool have been placed along the substantially cylindrical substrate at their respective positions, the method 600 may proceed to one or more of a step 630, a step 640, and/or a step 650 in which the first cutting head may be rotated about a first longitudinal axis of the first mill tool, the second cutting head may be rotated about a second longitudinal axis of the second mill tool, and the substantially cylindrical substrate may be rotated about a third longitudinal axis of the substantially cylindrical substrate.

Once the first mill tool, the second mill tool, and the substantially cylindrical substrate are all rotating about their respective axes, the method 600 may proceed a step 660 in which the first and/or the second cutting heads may be translated along a length of the substantially cylindrical substrate. Alternatively, or in addition thereto, the substantially cylindrical substrate may be translated with respect to the first and/or the second cutting heads.

As the first mill tool, the second mill tool, and/or the substantially cylindrical substrate are translated with respect to each other during rotation, the first helical thread may be formed in the substantially cylindrical substrate in a step 670, and/or the second helical thread may be formed in the substantially cylindrical substrate in a step 680 by the cutting heads of the first and second mill tools.

Once a desired plurality of helical threading has been formed in the substantially cylindrical substrate, the method 600 may end.

Any procedures/methods disclosed herein comprise one or more steps or actions for performing the described method. The method steps and/or actions may be interchanged with one another. In other words, unless a specific order of steps or actions is required for proper operation of the embodiment, the order and/or use of specific steps and/or actions may be modified.

Any of the fasteners described herein may be configured for removal and replacement during a revision procedure by simply unscrewing and removing the fastener from the bone/tissue in which the fastener resides. Moreover, the fasteners described herein may advantageously be removed from bone without removing any appreciable amount of bone during the removal process to preserve the bone. In this manner, implants may be mechanically integrated with the bone, while not being cemented to the bone or integrated via bony ingrowth, in order to provide an instant and removable connection between an implant and a bone. Accordingly, revision procedures utilizing the fasteners described herein can result in less trauma to the bone and improved patient outcomes.

Reference throughout this specification to "an embodiment" or "the embodiment" means that a particular feature, structure, or characteristic described in connection with that embodiment is included in at least one embodiment. Thus, the quoted phrases, or variations thereof, as recited throughout this specification are not necessarily all referring to the same embodiment.

Similarly, it should be appreciated that in the above description of embodiments, various features are sometimes grouped together in a single embodiment, Figure, or description thereof for the purpose of streamlining the present disclosure. This method of disclosure, however, is not to be interpreted as reflecting an intention that any embodiment requires more features than those expressly recited in that embodiment. Rather, inventive aspects lie in a combination of fewer than all features of any single foregoing disclosed embodiment.

Recitation of the term "first" with respect to a feature or element does not necessarily imply the existence of a second or additional such feature or element. Elements recited in means-plus-function format are intended to be construed in accordance with 35 U.S.C. § 112(f). It will be apparent to those having skill in the art that changes may be made to the details of the above-described embodiments without departing from the underlying principles set forth herein.

The phrases "connected to," "coupled to" and "in communication with" refer to any form of interaction between two or more entities, including mechanical, electrical, magnetic, electromagnetic, fluid, and thermal interaction. Two components may be functionally coupled to each other even though they are not in direct contact with each other. The term "coupled" can include components that are coupled to each other via integral formation, as well as components that are removably and/or non-removably coupled with each other. The term "abutting" refers to items that may be in direct physical contact with each other, although the items may not necessarily be attached together. The phrase "fluid communication" refers to two or more features that are connected such that a fluid within one feature is able to pass into another feature. Moreover, as defined herein the term "substantially" means within +/−20% of a target value, measurement, or desired characteristic.

While specific embodiments and applications of the present disclosure have been illustrated and described, it is to be understood that the scope of this disclosure is not limited to the precise configuration and components disclosed herein. Various modifications, changes, and variations which will be apparent to those skilled in the art may be made in the arrangement, operation, and details of the devices, systems, and methods disclosed herein.

What is claimed is:

1. An implantable bone anchor comprising:
a shaft comprising:
a minor diameter;
a proximal end;
a distal end; and
a longitudinal axis;
a first helical thread disposed about the shaft along the longitudinal axis between the proximal and distal ends of the shaft, the first helical thread comprising:
a first undercut surface;
a second undercut surface;
a third undercut surface; and
a fourth open surface; and
a second helical thread disposed about the shaft adjacent the first helical thread, the second helical thread comprising:
a fifth undercut surface;
a sixth undercut surface;
a seventh undercut surface; and
an eighth open surface;
wherein, when the implantable bone anchor is viewed in section along a plane containing the longitudinal axis of the shaft:
the first undercut surface, the third undercut surface, the sixth undercut surface, and the eighth open surface are angled towards the distal end of the shaft as they extend away from the longitudinal axis;
the second undercut surface, the fourth open surface, the fifth undercut surface, and the seventh undercut surface are angled towards the proximal end of the shaft as they extend away from the longitudinal axis;
the first undercut surface and the second undercut surface form a first concave undercut surface of the first helical thread that is open toward the proximal end of the shaft and extends from the minor diameter of the shaft to a first crest of the first helical thread; and
the fifth undercut surface and the sixth undercut surface form a second concave undercut surface of the second helical thread that is open toward the distal end of the shaft and extends from the minor diameter of the shaft to a second crest of the second helical thread.

2. The implantable bone anchor of claim 1, wherein:
when the implantable bone anchor is viewed in section along the plane containing the longitudinal axis of the shaft:
the first helical thread comprises at least one chevron shape oriented toward the distal end of the shaft; and
the second helical thread comprises at least one chevron shape oriented toward the proximal end of the shaft.

3. The implantable bone anchor of claim 2, wherein, when the implantable bone anchor is viewed in section along the plane containing the longitudinal axis of the shaft:
the at least one chevron shape of the first helical thread comprises a first plurality of chevron shapes oriented toward the distal end of the shaft; and
the at least one chevron shape of the second helical thread comprises a second plurality of chevron shapes oriented toward the proximal end of the shaft.

4. The implantable bone anchor of claim 3, wherein the first plurality of chevron shapes and the second plurality of chevron shapes are arranged in alternating succession along the shaft of the implantable bone anchor.

5. The implantable bone anchor of claim 1, wherein:
when the implantable bone anchor is viewed in section along the plane containing the longitudinal axis of the shaft:

the first helical thread comprises at least one partial crescent shape oriented toward the distal end of the shaft; and the second helical thread comprises at least one partial crescent shape oriented toward the proximal end of the shaft.

6. The implantable bone anchor of claim 5, wherein, when the implantable bone anchor is viewed in section along the plane containing the longitudinal axis of the shaft:

the at least one partial crescent shape of the first helical thread comprises a first plurality of partial crescent shapes oriented toward the distal end of the shaft; and the at least one partial crescent shape of the second helical thread comprises a second plurality of partial crescent shapes oriented toward the proximal end of the shaft.

7. The implantable bone anchor of claim 6, wherein the first plurality of partial crescent shapes and the second plurality of partial crescent shapes are arranged in alternating succession along the shaft of the implantable bone anchor.

8. A fastener comprising:
a shaft comprising:
a minor diameter;
a proximal end;
a distal end; and
a longitudinal axis; and
a plurality of helical threads disposed about the shaft along the longitudinal axis between the proximal and distal ends of the shaft, the plurality of helical threads comprising:
a first helical thread comprising:
a first concave undercut surface open toward the proximal end of the shaft; and
a first convex undercut surface facing toward the distal end of the shaft; and
a second helical thread comprising:
a second concave undercut surface open toward the distal end of the shaft; and
a second convex undercut surface facing toward the proximal end of the shaft;
wherein, when the fastener is viewed in section along a plane containing the longitudinal axis of the shaft:
the first concave undercut surface and the first convex undercut surface of the first helical thread each extend from the minor diameter of the shaft to a first crest of the first helical thread;
the second concave undercut surface and the second convex undercut surface of the second helical thread each extend from the minor diameter of the shaft to a second crest of the second helical thread;
a first interlocking space is formed intermediate the first concave undercut surface and the second concave undercut surface;
a second interlocking space is formed intermediate the first convex undercut surface and the second convex undercut surface; and
at least one of:
the first helical thread does not have mirror symmetry with itself across any plane perpendicular to the longitudinal axis of the shaft; and
the second helical thread does not have mirror symmetry with itself across any plane perpendicular to the longitudinal axis of the shaft.

9. The fastener of claim 8, wherein the plurality of helical threads comprises three helical threads.

10. The fastener of claim 8, wherein the plurality of helical threads comprises four helical threads.

11. The fastener of claim 8, wherein the plurality of helical threads comprises more than four helical threads.

12. The fastener of claim 8, wherein at least one of the first concave undercut surface, the first convex undercut surface, the second concave undercut surface, and the second convex undercut surface comprises at least one substantially flat surface.

13. The fastener of claim 8, wherein at least one of the first concave undercut surface, the first convex undercut surface, the second concave undercut surface, and the second convex undercut surface comprises at least one curved surface.

14. The fastener of claim 8, wherein:
when the fastener is viewed in section along the plane containing the longitudinal axis of the shaft:
the first helical thread comprises a first bent shape with a first intermediate portion oriented toward the distal end of the shaft; and
the second helical thread comprises a second bent shape with a second intermediate portion oriented toward the proximal end of the shaft.

15. The fastener of claim 8,
wherein each of the first interlocking space and the second interlocking space are configured to receive bone tissue therein; and
wherein each of the first interlocking space and the second interlocking space are shaped to interlock with the bone tissue to increase fixation of the fastener within the bone tissue.

16. The fastener of claim 15, wherein the first interlocking space is larger in size than the second interlocking space.

17. An implantable bone anchor comprising:
a shaft comprising:
a minor diameter;
a proximal end;
a distal end; and
a longitudinal axis;
a first helical thread disposed about the shaft along the longitudinal axis between the proximal and distal ends of the shaft, the first helical thread comprising:
a first concave undercut surface open toward the proximal end; and
a first convex undercut surface facing toward the distal end; and
a second helical thread disposed about the shaft adjacent the first helical thread, the second helical thread comprising:
a second concave undercut surface open toward the distal end, opposite the first concave undercut surface; and
a second convex undercut surface facing toward the proximal end, opposite the first convex undercut surface;
wherein, when the implantable bone anchor is viewed in section along a plane containing the longitudinal axis of the shaft:
a first interlocking space is formed intermediate the first concave undercut surface and the second concave undercut surface that extends to the minor diameter of the shaft;
a second interlocking space is formed intermediate the first convex undercut surface and the second convex undercut surface that extends to the same minor diameter of the shaft as the first interlocking space; and
at least one of:

the first helical thread does not have mirror symmetry with itself across any plane perpendicular to the longitudinal axis; and the second helical thread does not have mirror symmetry with itself across any plane perpendicular to the longitudinal axis.

18. The implantable bone anchor of claim 17, wherein, when the implantable bone anchor is viewed in section along the plane containing the longitudinal axis of the shaft:

the first concave undercut surface and the first convex undercut surface of the first helical thread form a plurality of first chevron shapes oriented toward the distal end.

19. The implantable bone anchor of claim 18, wherein, when the implantable bone anchor is viewed in section along the plane containing the longitudinal axis of the shaft:

the second concave undercut surface and the second convex undercut surface of the second helical thread form a plurality of second chevron shapes oriented toward the proximal end.

\* \* \* \* \*